US007871780B2

(12) United States Patent
Sung et al.

(10) Patent No.: US 7,871,780 B2
(45) Date of Patent: *Jan. 18, 2011

(54) GENOMIC MARKERS OF HEPATITIS B VIRUS ASSOCIATED WITH HEPATOCELLULAR CARCINOMA

(75) Inventors: Jao Yiu Joseph Sung, Ma On Shan (HK); Lik Yuen Chan, Shatin (HK); Kwok Wing Stephen Tsui, Ma On Shan (HK); Kwong Sak Leung, Shatin (HK); Shu Kam Tony Mok, Shatin (HK); Angeline Bartholomeusz, Victoria (AU); Wai Yee Nancy Leung, Happy Valley (HK); Kin Hong Lee, Hung Hom (HK)

(73) Assignees: The Chinese University of Hong Kong, Shatin, N.T. (HK); The Hospital Authority, Kowloon (HK)

( * ) Notice: Subject to any disclaimer, the term of this patent is extended or adjusted under 35 U.S.C. 154(b) by 0 days.

This patent is subject to a terminal disclaimer.

(21) Appl. No.: 12/208,256

(22) Filed: Sep. 10, 2008

(65) Prior Publication Data

US 2009/0023133 A1    Jan. 22, 2009

Related U.S. Application Data

(60) Division of application No. 11/019,426, filed on Dec. 20, 2004, now Pat. No. 7,439,020, which is a continuation-in-part of application No. 10/937,987, filed on Sep. 10, 2004, now abandoned.

(51) Int. Cl.
*C12Q 1/68* (2006.01)
*C07H 21/04* (2006.01)

(52) U.S. Cl. .................. 435/6; 536/23.1; 536/24.31; 536/24.32

(58) Field of Classification Search ................ None
See application file for complete search history.

(56) References Cited

PUBLICATIONS

Blackberg, Jonas et al.; "Mutations Within the Hepatitus B Virus Genome Among Chronic Hepatitis B Patients With Hepatocellular Carcinoma"; 2003, *Journal of Medical Virology*, vol. 71, pp. 18-23.
Chan, H L-Y et al.; "Genotype C hepatitis B virus infection is associated with an increased risk of hepatocellular carcinoma"; 2004, *Gut*, vol. 53, pp. 1494-1498.
Cougot, Delphine, et al., :"HBV Induced Carcinogenesis," 2005, *Journal of Clinical Virology*, vol. 34, Suppl. 1, pp. S75-S78.
Gao, Jidong et al.; "Close Relation between Hepatocellular Carcinoma and HBV Infection in North China"; 2004, *Chin. J. Hepatobiliary Surg.*, vol. 10, No. 6, 9 pages.
International Search Report from PCT/CN2005/001477, Dec. 15, 2005.
Kao, Jia-Horng, et al, "Basal Core Promoter Mutations of Hepatitis B Virus Increase the Risk of Hepatocellular Carcinoma in Hepatitis B Carriers," 2003, *Gastroenterology*, vol. 124, No. 2, pp. 327-334.
Lin, Xu et al., "Structural Analysis of 22 Full-Length Hepatitis B Virus Genomes Isolated from Patients with Hepatocellular Carcinoma"; 2004, *Chin. J. Oncol.*, vol. 26, No. 4, 12 pages.
Tsubota, Akihito, et al., "Genotype May Correlate With Liver Carcinogenesis and Tumor Characteristics in Cirrhotic Patients Infected with Hepatitis B Virus Subtype *adw*," 2001, *Journal of Medical Virology*, vol. 65, No. 2, pp. 257-265.
Yue, Feng-e et al.; "Relations Between Hepatocellular Carcinoma and HBV Infection"; 2001, *China J. Cancer Prev Treat.*, vol. 8, No. 6, 8 pages.
Zhu, Rong et al.; "Progress in Study on Relations between Hepatitis B Virus X Protein and Hepatocellular Carcinoma"; 2004, Foreign Medical Sciences Epidemiology Lemology, vol. 31, No. 4, 10 pages.

*Primary Examiner*—Bo Peng
(74) *Attorney, Agent, or Firm*—Townsend and Townsend and Crew LLP

(57) ABSTRACT

The present invention provides methods of predicting a predisposition of HBV-infected individuals to develop hepatacellular carcinoma (HCC).

14 Claims, 7 Drawing Sheets

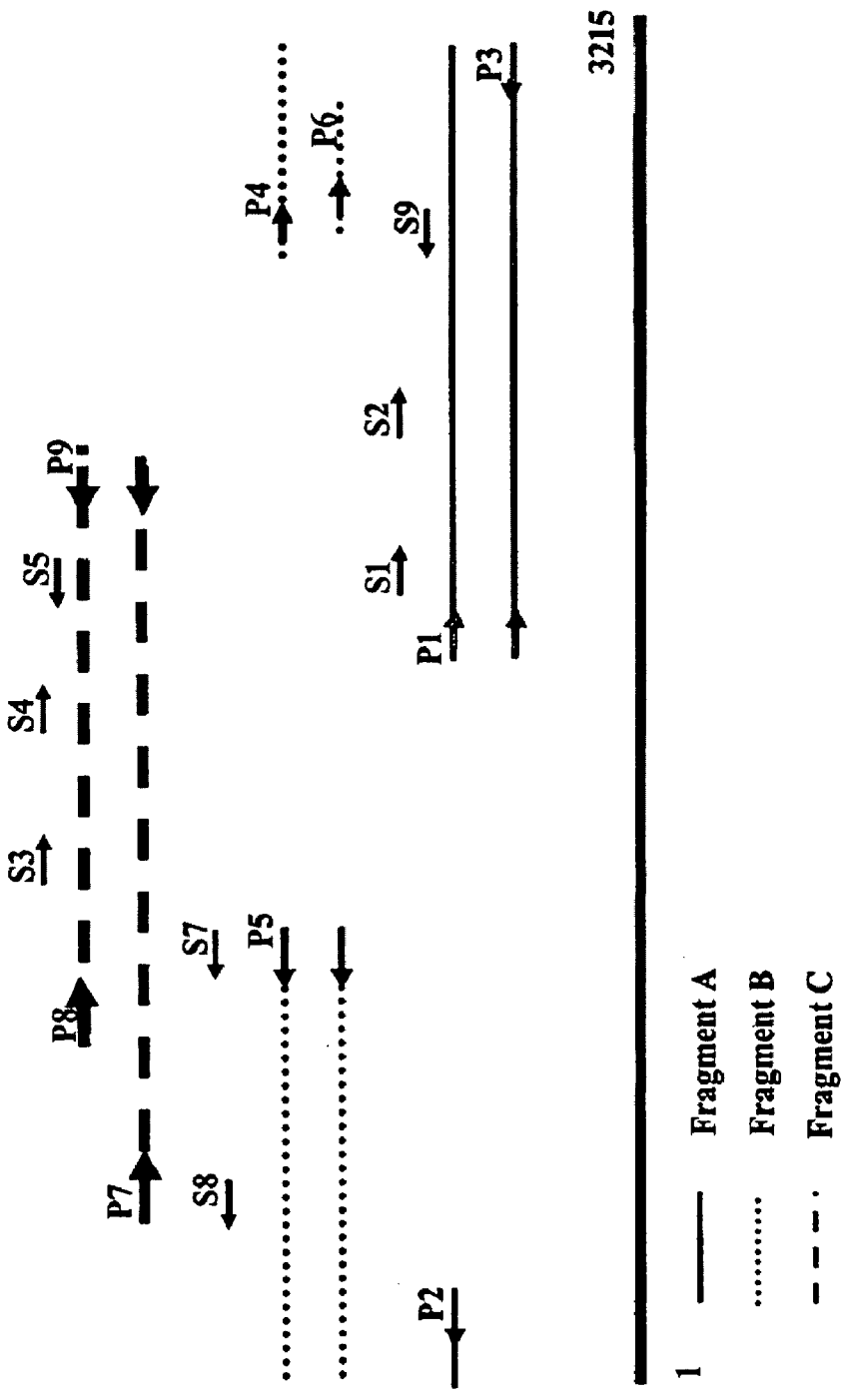

Figure 2A

```
            10         20         30         40         50         60
       CTCCACCACT TTCCACCAAA CTCTTCAAGA TCCCAGAGTC AGGGCCCTGT ACTTTCCTGC
            70         80         90        100        110        120
       TGGTGGCTCC AGTTCAGAAA CAGTGAGCCC TGCTCAGAAT ACTGTCTCTG CCATATCGTC
           130        140        150        160        170        180
       AATCTTATCG AAGACTGGGG ACCCTGTACC GAACATGGAG AACATCGCAT CAGGACTCCT
           190        200        210        220        230        240
       AGGACCCCTG CTCGTGTTAC AGGCGGGGTT TTTCTCGTTG ACAAAAATCC TCACAATACC
           250        260        270        280        290        300
       ACAGAGTCTA GACTCGTGGT GGACTTCTCT CAATTTTCTA GGGGAAACAC CCGTGTGTCT
           310        320        330        340        350        360
       TGGCCAAAAT TCGCAGTCCC AAATCTCCAG TCACTCACCA ACCTGTTGTC CTCCAATTTG
           370        380        390        400        410        420
       TCCTGGTTAT CGCTGGATGT GTCTGCGGCG TTTTATCATC TTCCTCTGCA TCCTGCTGCT
           430        440        450        460        470        480
       ATGCCTCATC TTCTTGTTGG TTCTTCTGGA CTATCAAGGT ATGTTGCCCG TTTGTCCTCT
           490        500        510        520        530        540
       AATTCCAGGA TCATCAACGA CCAGCACCGG ACCATGCAAA ACCTGCACAA CTCCTGCTCA
           550        560        570        580        590        600
       AGGAACCTCT ATGTTTCCCT CATGTTGCTG TACAAAACCT ACGGACGGAA ATTGCACCTG
           610        620        630        640        650        660
       TATTCCCATC CCATCATCTT GGGCTTTCGC AAAATACCTA TGGGAGTGGG CCTCAGTCCG
           670        680        690        700        710        720
       TTTCTCTTGG CTCAGTTTAC TAGTGCCATT TGTTCAGTGG TTCGTAGGGC TTTCCCCCAC
           730        740        750        760        770        780
       TGTCTGGCTT TCAGTTATAT GGATGATGTG GTTTTGGGGG CCAAGTCTGT ACAACATCTT
           790        800        810        820        830        840
       GAGTCCCTTT ATGCCGCTGT TACCAATTTT CTTTTGTCTT TGGGTATACA TTTAAACCCT
           850        860        870        880        890        900
       CACAAAACAA AAAGATGGGG ATATTCCCTT AACTTCATGG GATATGTAAT TGGGAGTTGG
           910        920        930        940        950        960
       GGCACATTGC CACAGGAACA TATTGTACAA AAAATCAAAA TGTGTTTTCG GAAACTTCCT
           970        980        990       1000       1010       1020
       GTAAATAGAC CTATTGATTG GAAAGTATGT CAACGAATTG TGGGTCTTTT GGGGTTTGCC
          1030       1040       1050       1060       1070       1080
       GCCCCTTTCA CGCAATGTGG ATATCCTGCT TTAATGCCTT TATATGCATG TATTCAAGCA
          1090       1100       1110       1120       1130       1140
       AAACAGGCTT TTACTTTCTC GCCAACTTAC AAGGCCTTTC TAAGTAAACA GTATCTGAAC
          1150       1160       1170       1180       1190       1200
       CTTTACCCCG TTGCTCGGCA ACGGCCTGGT CTGTGCCAAG TGTTTGCTGA CGCAACCCCC
          1210       1220       1230       1240       1250       1260
       ACTGGTTGGG GCTTGGCCAT AGGCCATCAG CGCATGCGTG GAACCTTTGG GTCTCCTCTG
          1270       1280       1290       1300       1310       1320
       CCGATCCATA CTGCGGAACT CCTAGCCGCT TGTTTTGCTC GCAGCAGGTC TGGAGCAAGA
          1330       1340       1350       1360       1370       1380
       CTCATCGGGA CTGACAATTC TGTCGTGCTC TCCCGCAAGT ATACATCATT TCCATGGCTG
          1390       1400       1410       1420       1430       1440
       CTAGGCTGTG CTGCCAACTG GATCCTACGC GGGACGTCCT TTGTTTACGT CCCGTCGGCG
          1450       1460       1470       1480       1490       1500
       CTGAATCCCG CGGACGACCC CTCCCGGGGC CGCTTGGGGC TCTACCGCCC GCTTCTCCGC
          1510       1520       1530       1540       1550       1560
       CTATTGTACC GACCGACCAC GGGGCGCACC TCTCTTTACG CGGACTCCCC GTCTGTGCCT
          1570       1580       1590       1600       1610       1620
       TCTCATCTGC CGGACCGTGT GCACTTCGCT TCACCTCTGC ACGTCGCATG GAGACCACCG
          1630       1640       1650       1660       1670       1680
       TGAACGCCCA CGGGAACCTG CCCAAGGTCT TGCATAAGAG AACTCTTGGA CTTTCAGCAA
```

Figure 2B

```
      1690       1700       1710       1720       1730       1740
TGTCAACGAC CGACCTTGAG GCATACTTCA AAGACTGTGT GTTTACTGAG TGGGAGGAGT
      1750       1760       1770       1780       1790       1800
TGGGGGAGGA GATTAGGTTA AAGGTCTTTG TACTAGGAGG CTGTAGGCAT AAATTGGTGT
      1810       1820       1830       1840       1850       1860
GTTCACCAGC ACCATGCAAC TTTTTCACCT CTGCCTAATC ATCTCATGTT CATGTCCTAC
      1870       1880       1890       1900       1910       1920
TGTTCAAGCC TCCAAGCTGT GCCTTGGGTG GCTTTGGGGC ATGGACATTG ACCCGTATAA
      1930       1940       1950       1960       1970       1980
AGAATTTGGA GCTTCTGTGG AGTTACTCTC TTTTTTGCCT TCTGACTTCT TTCCTTCTAT
      1990       2000       2010       2020       2030       2040
TCGAGATCTC CTCGACACCG CCTCTGCTCT GTATCGGGAG GCCTTAGAGT CTCCGGAACA
      2050       2060       2070       2080       2090       2100
TTGTTCACCT CACCATACGG CACTCAGGCA AGCTATTCTG TGTTGGGGTG AGTTAATGAA
      2110       2120       2130       2140       2150       2160
TCTAGCCACC TGGGTGGGAA GTAATTTGGA AGATCCAGCA TCCAGGGAAT TAGTAGTCAG
      2170       2180       2190       2200       2210       2220
CTATGTCAAC GTTAATATGG GCCTAAAACT CAGACAAATA TTGTGGTTTC ACATTTCCTG
      2230       2240       2250       2260       2270       2280
TCTTACTTTT GGGAGAGAAA CTGTTCTTGA ATATTTGGTG TCTTTTGGAG TGTGGATTCG
      2290       2300       2310       2320       2330       2340
CACTCCTCCT GCATATAGAC CACAAAATGC CCCTATCTTA TCAACACTTC CGGAAACTAC
      2350       2360       2370       2380       2390       2400
TGTTGTTAGA CGAAGATGCA GGTCCCCTAG AAGAAGAACT CCCTCGCCTC GCAGACGAAG
      2410       2420       2430       2440       2450       2460
GTCTCAATCG CCGCGTCGCA GAAGATCTCA ATCTCGGGAA TCTCAATGTT AGTATTCCTT
      2470       2480       2490       2500       2510       2520
GGACACATAA GGTGGGAAAC TTTACGGGGC TTTATTCTTC TACGGTACCT TGCTTTAATC
      2530       2540       2550       2560       2570       2580
CTAAATGGCA AACTCCTTCT TTTCCTGACA TTCATTTGCA GGAGGACATT GTTGATAGAT
      2590       2600       2610       2620       2630       2640
GCAAGCAATT TGTGGGGCCC CTTACAGTAA ATGAAAACAG GAGACTAAAA TTAATTATGC
      2650       2660       2670       2680       2690       2700
CTGCTAGGTT TTATCCCAAT GTTACTAAAT ATTTGCCCTT AGATAAAGGG ATCAAACCGT
      2710       2720       2730       2740       2750       2760
ATTATCCAGA GTATGTAGTT AATCATTACT TTCAGACGCG ACATTATTTA CACACTCTTT
      2770       2780       2790       2800       2810       2820
GGAAGGCGGG GATCTTATAT AAAAGAGAGT CCACACGTAG CGCCTCATTT TGCGGGTCAC
      2830       2840       2850       2860       2870       2880
CATATTCTTG GGAACAAGAT CTACAGCATG GGAGGTTGGT CTTCCAAACC TCGAAAGGC
      2890       2900       2910       2920       2930       2940
ATGGGGACAA ATCTTTCTGT CCCCAATCCC CTGGGATTCT TCCCCGATCA TCAGTTGGAC
      2950       2960       2970       2980       2990       3000
CCTGCATTCA AAGCCAACTC AGAAAATCCA GATTGGGACC TCAACCCGCA CAAGGACAAC
      3010       3020       3030       3040       3050       3060
TGGCCGGACG CCAACAAGGT GGGAGTGGGA GCATTCGGGC CAGGGTTCAC CCCTCCCCAT
      3070       3080       3090       3100       3110       3120
GGGGGACTGT TGGGGTGGAG CCCTCAAGCT CAGGGCCTAC TCACAACTGT GCCAGCAGCT
      3130       3140       3150       3160       3170       3180
CCTCCTCCTG CCTCCACCAA TCGGCAGTCA GGAAGGCAGC CTACTCCCTT ATCTCCACCT
      3190       3200       3210       3220
CTAAGGGACA CTCATCCTCA GGCCATGCAG TGGAA
```

Figure 3A

```
            10         20         30         40         50         60
      CTCCAGCACA TTCCACCAAG CTCTGCTAGA TCCCAGAGTG AGGGGCCTAT ACCTTCCTGC
            70         80         90        100        110        120
      TGGTGGCTCC AGTTCCGGAA CAGTAAACCC TGTTCCGACT ACTGCCTCTC CCATATCGTC
           130        140        150        160        170        180
      AATCTTCTCG AGGACTGGGG ACCCTGCACC GAATATGGAG AGCACCACAT CAGGATTCCT
           190        200        210        220        230        240
      AGGACCCCTG CTCGTGTTAC AGGCGGGGTT TTTCTTGTTG ACAAGAATCC TCACAATACC
           250        260        270        280        290        300
      ACAGAGTCTA GACTCGTGGT GGACTTCTCT CAATTTTCTA GGGGGAGCAC CCACGTGTCC
           310        320        330        340        350        360
      TGGCCAAAAT TTGCAGTCCC CAACCTCCAA TCACTCACCA ACCTCTTGTC CTCCAATTTG
           370        380        390        400        410        420
      TCCTGGTTAT CGCTGGATGT GTCTGCGGCG TTTTATCATC TTCCTCTTCA TCCTGCTGCT
           430        440        450        460        470        480
      ATGCCTCATC TTCTTGTTGG TTCTTCTGGA CTACCAAGGT ATGTTGCCCG TTTGTCCTCT
           490        500        510        520        530        540
      ACTTCCAGGA ACATCAACTA CCAGCACGGG ACCATGCAAG ACCTGCACGA TTCCTGCTCA
           550        560        570        580        590        600
      AGGAACCTCT ATGTTTCCCT CTTGTTGCTG TACAAAACCT TCGGACGGAA ATTGCACTTG
           610        620        630        640        650        660
      TATTCCCATC CCATCATCTT GGGCTTTCGC AAGATTCCTA TGGGAGTGGG CCTCAGTCCG
           670        680        690        700        710        720
      TTTCTCCTGG CTCAGTTTAC TAGTGCCATT TGTTCAGTGG TTCGTAGGGC TTTCCCCCAC
           730        740        750        760        770        780
      TGTTTGGCTT TCAGTTATAT GGATGATGTG GTATTGGGGG CCAAGTCTGT ACAACATCTT
           790        800        810        820        830        840
      GAATCCCTTT ATACCGCTAT TACCAATTTT CTTGTGTCTT TGGGTATACA TTTAAACCCT
           850        860        870        880        890        900
      AATAAAACCA AACGTTGGGG CTACTCCCTT AACTTCATGG GATATGTAAT TGGAAGTTGG
           910        920        930        940        950        960
      GGTACCTTGC CACAGGAACA TATTGTACAA AAAATCAAAC AATGTTTTCG AAAACTTCCT
           970        980        990       1000       1010       1020
      ATAAATAGAC CTATTGATTG GAAAGTATGT CAAAGAATTG TGGGTCTTTT GGGTTTTGCC
          1030       1040       1050       1060       1070       1080
      GCTCCCTTTA CACAATGTGG TTACCCAGCA TTAATGCCTT TATATGCATG TATACAAGCT
          1090       1100       1110       1120       1130       1140
      AAACAGGCTT TCACTTTCTC GCCAACTTAC AAGGCCTTTC TGTATAAACA ATATCTGAAC
          1150       1160       1170       1180       1190       1200
      CTTTACCCCG TTGCTCGGCA ACGGTCAGGT CTTTGCCAAG TGTTTGCTGA CGCAACCCCC
          1210       1220       1230       1240       1250       1260
      ACTGGTTGGG GCTTGGCCAT GGGCCATCAG CGCATGCGTG GAACCTTTGT GGCTCCTCTG
          1270       1280       1290       1300       1310       1320
      CCGATCCATA CTGCGGAACT CCTAGCAGCT TGTTTTGCTC GCAGCCGGTC TGGAGCAAAC
          1330       1340       1350       1360       1370       1380
      CTTATCGGCA CCGACAACTC TGTTGTCCTC TCTCGGAAAT ACACCTCTTT TCCATGGCTG
          1390       1400       1410       1420       1430       1440
      CTAGGCTGTG CTGCCAACTG GATCCTGCGC GGGACGTCCT TTGTCTACGT CCCGTCGGCG
          1450       1460       1470       1480       1490       1500
      CTGAATCCCG CGGACGACCC GTCTCGGGGT CGTTTGGGAC TCTACCGTCC CCTTCTCCGT
          1510       1520       1530       1540       1550       1560
      CTGCCGTTCC GGCCGACCAC GGGGCGCACC TCTCTTTACG CGGACTCCCC GTCTGTGCCT
          1570       1580       1590       1600       1610       1620
      TCTCATCTGC CGGACCGTGT GCACTTCGCT TCACCTCTGC ACGTCGCATG GAGACCACCG
          1630       1640       1650       1660       1670       1680
      TGAACGCCCG CCAGGTCTTG CCTAAGGTCT TACATAAGAG GACTCTTGGA CTCTCAGCAA
```

Figure 3B

```
         1690        1700       1710       1720       1730       1740
    TGTCAACGAC  CGACCTTGAG GCATACTTCA AAGACTGTGT ATTTAAGGAC TGGGAGGAGT
         1750        1760       1770       1780       1790       1800
    TGGGGGAGGA  GATTAGGTTA ATGATCTTTG TACTGGGAGG CTGTAGGCAT AAATTGGTCT
         1810        1820       1830       1840       1850       1860
    GTTCACCAGC  ACCATGCAAC TTTTTCACCT CTGCCTAATC ATCTCATGTT CATGTTCCAC
         1870        1880       1890       1900       1910       1920
    TGTTCAAGCC  TCCAAGCTGT GCCTTGGGTG GCTTTGGGGC ATGGACATTG ACCCGTATAA
         1930        1940       1950       1960       1970       1980
    AGAATTTGGA  GCTTCTGTGG AGTTACTCTC TTTTTTGCCT TCTGACTTTT TTCCTTCTAT
         1990        2000       2010       2020       2030       2040
    TCGTGATCTC  CTCGACACCG CCTCTGCTCT GTATCGGGAG GCCTTAGAGT CTCCGGAACA
         2050        2060       2070       2080       2090       2100
    TTGTTCACCT  CACCATACAG CACTAAGGCA AGCTATTCTG TGTTGGGGTG AGTTGATGAA
         2110        2120       2130       2140       2150       2160
    TCTGGCCACC  TGGGTGGGAA GTAATTTGGA AGACCCGGCA TCCAGGGAAT TAGTAGTAAG
         2170        2180       2190       2200       2210       2220
    CTATGTCAAT  GTTAATATGG GCCTAAAAAT CAGACAACTA TTGTGGTTTC ACATTTCCTG
         2230        2240       2250       2260       2270       2280
    TCTTACTTTT  GGAAGAGAAA CTGTTCTTGA GTATTTGGTG TCTTTTGGAG TGTGGATTCG
         2290        2300       2310       2320       2330       2340
    CACTCCTCCC  GCTTACAGAC CACCAAATGC CCCTATCTTA TCAACACTTC CGGAAACTAC
         2350        2360       2370       2380       2390       2400
    TGTTGTTAGA  CGACGAGGCA GGTCCCCTAG AAGAAGAACT CCCTCGCCTC GCAGACGAAG
         2410        2420       2430       2440       2450       2460
    GTCTCAATCG  CCGCGTCGCA GAAGATCTCA GTCTCGGGAA TCTCAATGTT AGTATCCCTT
         2470        2480       2490       2500       2510       2520
    GGACTCATAA  GGTGGGAAAC TTTACTGGGC TTTATTCTTC TACTGTACCT GTCTTTAATC
         2530        2540       2550       2560       2570       2580
    CTGAATGGCA  AACTCCCTCT TTTCCTCACA TTCATTTGAA AGAGGATATT ATCAATAGAT
         2590        2600       2610       2620       2630       2640
    GTCAACAATA  TGTGGGCCCT CTTACAGTTA ACGAAAAAAG GAGATTAAAA TTGATCATGC
         2650        2660       2670       2680       2690       2700
    CTGCTAGGTT  CTATCCTAAC CTTACTAAAT ATTTGCCCTT AGATAAAGGC ATCAAACCTT
         2710        2720       2730       2740       2750       2760
    ATTATCCTGA  ACATATAGTT AATCATTACT TCCAAACTAG GCATTATTTA CATACTCTGT
         2770        2780       2790       2800       2810       2820
    GGAAGGCTGG  TATTTTATAT AAGAGAGAAA CTACTCGCAG CGCCTCATTT TGTGGGTCAC
         2830        2840       2850       2860       2870       2880
    CATATTCTTG  GGAACAAGAG CTACAGCATG GGAGGTTGGT CTTCCAAACC TCGACAAGGC
         2890        2900       2910       2920       2930       2940
    ATGGGGACGA  ATCTTTCCGT TCCCAATCCT CTGGGATTCT TTCCCGGTCA CCAGTTGGAC
         2950        2960       2970       2980       2990       3000
    CCGACATTCG  GAGCCAATTC AAACAATCCA GATTGGGACT TCAACCCCAA CAAGGATCAA
         3010        3020       3030       3040       3050       3060
    TGGCCAGCGG  CAAACCAGGT AGGAGTGGGA TCATTCGGGC CGGGGTTCAC TCCACCACAC
         3070        3080       3090       3100       3110       3120
    GGCAATCTTT  TGGGGTGGAG CCCTCAGGCT CAGGGCATAT TGACAACAGT ACCAGCAGCG
         3130        3140       3150       3160       3170       3180
    CCTCCTCCTG  CCTCCACCAA TCGGCAGTCA GGAAGAAAGC CTACTCCCAT CTCTCCACCT
         3190        3200       3210       3220
    CTAAGAGACA  GTCATCCTCA GGCCATGCAA TGGAA
```

Figure 4A

```
          10         20         30         40         50         60
  CTCCAGCACA TTCCACCAAG CTCTGCTAGA TCCCAGAGTG AGGGGCCTAT ACCTTCCTGC
          70         80         90        100        110        120
  TGGTGGCTCC AGTTCCGGAA CAGTAAACCC TGTTCCGACT ACTGCCTCTC CCATATCGTC
         130        140        150        160        170        180
  AATCTTCTCG AGGACTGGGG ACCCTGCACC GAATATGGAG AGCACCACAT CAGGATTCCT
         190        200        210        220        230        240
  AGGACCCCTG CTCGTGTTAC AGGCGGGGTT TTTCTTGTTG ACAAGAATCC TCACAATACC
         250        260        270        280        290        300
  ACAGAGTCTA GACTCGTGGT GGACTTCTCT CAATTTTCTA GGGGGAGCAC CCACGTGTCC
         310        320        330        340        350        360
  TGGCCAAAAT TTGCAGTCCC CAACCTCCAA TCACTCACCA ACCTCTTGTC CTCCAATTTG
         370        380        390        400        410        420
  TCCTGGTTAT CGCTGGATGT GTCTGCGGCG TTTTATCATC TTCCTCTTCA TCCTGCTGCT
         430        440        450        460        470        480
  ATGCCTCATC TTCTTGTTGG TTCTTCTGGA CTACCAAGGT ATGTTGCCCG TTTGTCCTCT
         490        500        510        520        530        540
  ACTTCCAGGA ACATCAACTA CCAGCACGGG ACCATGCAAG ACCTGCACGA TTCCTGCTCA
         550        560        570        580        590        600
  AGGAACCTCT ATGTTTCCCT CTTGTTGCTG TACAAAACCT TCGGACGGAA ATTGCACTTG
         610        620        630        640        650        660
  TATTCCCATC CCATCATCTT GGGCTTTCGC AAGATTCCTA TGGAGTGGG CCTCAGTCCG
         670        680        690        700        710        720
  TTTCTCCTGG CTCAGTTTAC TAGTGCCATT TGTTCAGTGG TTCGTAGGGC TTTCCCCCAC
         730        740        750        760        770        780
  TGTTTGGCTT TCAGTTATAT GGATGATGTG GTATTGGGGG CCAAGTCTGT ACAACATCTT
         790        800        810        820        830        840
  GAATCCCTTT ATACCGCTAT TACCAATTTT CTTGTGTCTT TGGGTATACA TTTAAACCCT
         850        860        870        880        890        900
  AATAAAACCA AACGTTGGGG CTACTCCCTT AACTTCATGG GATATGTAAT TGGAAGTTGG
         910        920        930        940        950        960
  GGTACCTTGC CACAGGAACA TATTGTACAA AAAATCAAAC AATGTTTTCG AAAACTTCCT
         970        980        990       1000       1010       1020
  ATAAATAGAC CTATTGATTG GAAAGTATGT CAAAGAATTG TGGGTCTTTT GGGTTTTGCC
        1030       1040       1050       1060       1070       1080
  GCTCCCTTTA CACAATGTGG TTACCCAGCA TTAATGCCTT TATATGCATG TATACAAGCT
        1090       1100       1110       1120       1130       1140
  AAACAGGCTT TCACTTTCTC GCCAACTTAC AAGGCCTTTC TGTATAAACA ATATCTGAAC
        1150       1160       1170       1180       1190       1200
  CTTTACCCCG TTGCTCGGCA ACGGTCAGGT CTTTGCCAAG TGTTTGCTGA CGCAACCCCC
        1210       1220       1230       1240       1250       1260
  ACTGGTTGGG GCTTGGCCAT GGGCCATCAG CGCATGCGTG GAACCTTTGT GGCTCCTCTG
        1270       1280       1290       1300       1310       1320
  CCGATCCATA CTGCGGAACT CCTAGCAGCT TGTTTTGCTC GCAGCCGGTC TGGAGCAAAC
        1330       1340       1350       1360       1370       1380
  CTTATCGGCA CCGACAACTC TGTTGTCCTC TCTCGGAAAT ACACCTCTTT TCCATGGCTG
        1390       1400       1410       1420       1430       1440
  CTAGGCTGTG CTGCCAACTG GATCCTGCGC GGGACGTCCT TTGTCTACGT CCCGTCGGCG
        1450       1460       1470       1480       1490       1500
  CTGAATCCCG CGGACGACCC GTCTCGGGGT CGTTTGGGAC TCTACCGTCC CCTTCTCCGT
        1510       1520       1530       1540       1550       1560
  CTGCCGTTCC GGCCGACCAC GGGGCGCACC TCTCTTTACG CGGACTCCCC GTCTGTGCCT
        1570       1580       1590       1600       1610       1620
  TCTCATCTGC CGGACCGTGT GCACTTCGCT TCACCTCTGC ACGTCGCATG GAGACCACCG
        1630       1640       1650       1660       1670       1680
  TGAACGCCCG CCAGGTCTTG CCTAAGGTCT TACATAAGAG GACTCTTGGA CTCTCAGCAA
```

Figure 4B

```
              1690       1700       1710       1720       1730       1740
         TGTCAACGAC CGACCTTGAG GCATACTTCA AAGACTGTGT ATTTAAGGAC TGGGAGGAGT
              1750       1760       1770       1780       1790       1800
         TGGGGAGGA GATTAGGTTA ATGATCTTTG TACTGGGAGG CTGTAGGCAT AAATTGGTCT
              1810       1820       1830       1840       1850       1860
         GTTCACCAGC ACCATGCAAC TTTTTCACCT CTGCCTAATC ATCTCATGTT CATGTTCCAC
              1870       1880       1890       1900       1910       1920
         TGTTCAAGCC TCCAAGCTGT GCCTTGGGTG GCTTGGGGC ATGGACATTG ACCCGTATAA
              1930       1940       1950       1960       1970       1980
         AGAATTTGGA GCTTCTGTGG AGTTACTCTC TTTTTTGCCT TCTGACTTTT TTCCTTCTAT
              1990       2000       2010       2020       2030       2040
         TCGTGATCTC CTCGACACCG CCTCTGCTCT GTATCGGGAG GCCTTAGAGT CTCCGGAACA
              2050       2060       2070       2080       2090       2100
         TTGTTCACCT CACCATACAG CACTAAGGCA AGCTATTCTG TGTTGGGGTG AGTTGATGAA
              2110       2120       2130       2140       2150       2160
         TCTGGCCACC TGGGTGGGAA GTAATTTGGA AGACCCGGCA TCCAGGGAAT TAGTAGTAAG
              2170       2180       2190       2200       2210       2220
         CTATGTCAAT GTTAATATGG GCCTAAAAAT CAGACAACTA TTGTGGTTTC ACATTTCCTG
              2230       2240       2250       2260       2270       2280
         TCTTACTTTT GGAAGAGAAA CTGTTCTTGA GTATTTGGTG TCTTTTGGAG TGTGGATTCG
              2290       2300       2310       2320       2330       2340
         CACTCCTCCC GCTTACAGAC CACCAAATGC CCCTATCTTA TCAACACTTC CGGAAACTAC
              2350       2360       2370       2380       2390       2400
         TGTTGTTAGA CGACGAGGCA GGTCCCCTAG AAGAAGAACT CCCTCGCCTC GCAGACGAAG
              2410       2420       2430       2440       2450       2460
         GTCTCAATCG CCGCGTCGCA GAAGATCTCA GTCTCGGGAA TCTCAATGTT AGTATCCCTT
              2470       2480       2490       2500       2510       2520
         GGACTCATAA GGTGGGAAAC TTTACTGGGC TTTATTCTTC TACTGTACCT GTCTTTAATC
              2530       2540       2550       2560       2570       2580
         CTGAATGGCA AACTCCCTCT TTTCCTCACA TTCATTTGAA AGAGGATATT ATCAATAGAT
              2590       2600       2610       2620       2630       2640
         GTCAACAATA TGTGGGCCCT CTTACAGTTA ACGAAAAAAG GAGATTAAAA TTGATCATGC
              2650       2660       2670       2680       2690       2700
         CTGCTAGGTT CTATCCTAAC CTTACTAAAT ATTTGCCCTT AGATAAAGGC ATCAAACCTT
              2710       2720       2730       2740       2750       2760
         ATTATCCTGA ACATATAGTT AATCATTACT TCCAAACTAG GCATTATTTA CATACTCTGT
              2770       2780       2790       2800       2810       2820
         GGAAGGCTGG TATTTTATAT AAGAGAGAAA CTACTCGCAG CGCCTCATTT TGTGGGTCAC
              2830       2840       2850       2860       2870       2880
         CATATTCTTG GGAACAAGAG CTACAGCATG GGAGGTTGGT CTTCCAAACC TCGACAAGGC
              2890       2900       2910       2920       2930       2940
         ATGGGACGA ATCTTTCCGT TCCCAATCCT CTGGGATTCT TTCCCGGTCA CCAGTTGGAC
              2950       2960       2970       2980       2990       3000
         CCGACATTCG GAGCCAATTC AAACAATCCA GATTGGGACT TCAACCCCAA CAAGGATCAA
              3010       3020       3030       3040       3050       3060
         TGGCCAGCGG CAAACCAGGT AGGAGTGGGA TCATTCGGGC CGGGGTTCAC TCCACCACAC
              3070       3080       3090       3100       3110       3120
         GGCAATCTTT TGGGGTGGAG CCCTCAGGCT CAGGGCATAT TGACAACAGT ACCAGCAGCG
              3130       3140       3150       3160       3170       3180
         CCTCCTCCTG CCTCCACCAA TCGGCAGTCA GGAAGAAAGC CTACTCCCAT CTCTCCACCT
              3190       3200       3210       3220
         CTAAGAGACA GTCATCCTCA GGCCATGCAA TGGAA
```

SEQUENCE LISTING

<160> NUMBER OF SEQ ID NOS: 21

<210> SEQ ID NO 1
<211> LENGTH: 3215
<212> TYPE: DNA
<213> ORGANISM: Hepatitis B virus
<220> FEATURE:
<223> OTHER INFORMATION: exemplary HBV genotype B isolate

<400> SEQUENCE: 1

| | | | | | | |
|---|---|---|---|---|---|---|
| ctccaccact | ttccaccaaa | ctcttcaaga | tcccagagtc | agggccctgt | actttcctgc | 60 |
| tggtggctcc | agttcagaaa | cagtgagccc | tgctcagaat | actgtctctg | ccatatcgtc | 120 |
| aatcttatcg | aagactgggg | accctgtacc | gaacatggag | aacatcgcat | caggactcct | 180 |
| aggacccctg | ctcgtgttac | aggcggggtt | tttctcgttg | acaaaaatcc | tcacaatacc | 240 |
| acagagtcta | gactcgtggt | ggacttctct | caattttcta | ggggaaacac | ccgtgtgtct | 300 |
| tggccaaaat | tcgcagtccc | aaatctccag | tcactcacca | acctgttgtc | ctccaatttg | 360 |
| tcctggttat | cgctggatgt | gtctgcggcg | ttttatcatc | ttcctctgca | tcctgctgct | 420 |
| atgcctcatc | ttcttgttgg | ttcttctgga | ctatcaaggt | atgttgcccg | tttgtcctct | 480 |
| aattccagga | tcatcaacga | ccagcaccgg | accatgcaaa | acctgcacaa | ctcctgctca | 540 |
| aggaacctct | atgtttccct | catgttgctg | tacaaaacct | acggacggaa | attgcacctg | 600 |
| tattcccatc | ccatcatctt | gggctttcgc | aaaataccta | tgggagtggg | cctcagtccg | 660 |
| tttctcttgg | ctcagtttac | tagtgccatt | tgttcagtgg | ttcgtagggc | tttcccccac | 720 |
| tgtctggctt | tcagttatat | ggatgatgtg | gttttggggg | ccaagtctgt | acaacatctt | 780 |
| gagtcccttt | atgccgctgt | taccaatttt | cttttgtctt | tgggtataca | tttaaaccct | 840 |
| cacaaaacaa | aaagatgggg | atattccctt | aacttcatgg | gatatgtaat | tgggagttgg | 900 |
| ggcacattgc | cacaggaaca | tattgtacaa | aaaatcaaaa | tgtgttttcg | gaaacttcct | 960 |
| gtaaatagac | ctattgattg | gaaagtatgt | caacgaattg | tgggtctttt | ggggtttgcc | 1020 |
| gcccctttca | cgcaatgtgg | atatcctgct | ttaatgcctt | tatatgcatg | tattcaagca | 1080 |
| aaacaggctt | ttactttctc | gccaacttac | aaggcctttc | taagtaaaca | gtatctgaac | 1140 |
| ctttaccccg | ttgctcggca | acggcctggt | ctgtgccaag | tgtttgctga | cgcaaccccc | 1200 |
| actggttggg | gcttggccat | aggccatcag | cgcatcgtg | gaacctttgg | gtctcctctg | 1260 |
| ccgatccata | ctgcggaact | cctagccgct | tgttttgctc | gcagcaggtc | tggagcaaga | 1320 |
| ctcatcggga | ctgacaattc | tgtcgtgctc | tcccgcaagt | atacatcatt | tccatggctg | 1380 |

```
ctaggctgtg ctgccaactg gatcctacgc gggacgtcct ttgtttacgt cccgtcggcg    1440
ctgaatcccg cggacgaccc ctcccggggc cgcttggggc tctaccgccc gcttctccgc    1500
ctattgtacc gaccgaccac ggggcgcacc tctctttacg cggactcccc gtctgtgcct    1560
tctcatctgc cggaccgtgt gcacttcgct tcacctctgc acgtcgcatg gagaccaccg    1620
tgaacgccca cggaacctg cccaaggtct tgcataagag aactcttgga ctttcagcaa     1680
tgtcaacgac cgaccttgag gcatacttca agactgtgt gtttactgag tgggaggagt     1740
tgggggagga gattaggtta aaggtctttg tactaggagg ctgtaggcat aaattggtgt    1800
gttcaccagc accatgcaac ttttcacct ctgcctaatc atctcatgtt catgtcctac     1860
tgttcaagcc tccaagctgt gccttgggtg ctttgggc atggacattg acccgtataa      1920
agaatttgga gcttctgtgg agttactctc ttttttgcct tctgacttct ttccttctat    1980
tcgagatctc ctcgacaccg cctctgctct gtatcgggag gccttagagt ctccggaaca    2040 tgttcacct caccatacgg cactcaggca agctattctg tgttggggtg agttaatgaa     2100
tctagccacc tgggtgggaa gtaatttgga agatccagca tccagggaat tagtagtcag    2160
ctatgtcaac gttaatatgg gcctaaaact cagacaaata ttgtggtttc acatttcctg    2220
tcttactttt gggagagaaa ctgttcttga atatttggtg tcttttggag tgtggattcg    2280
cactcctcct gcatatagac cacaaaatgc ccctatctta tcaacacttc cggaaactac    2340
tgttgttaga cgaagatgca ggtccctag aagaagaact ccctcgcctc gcagacgaag     2400
gtctcaatcg ccgcgtcgca gaagatctca atctcggaa tctcaatgtt agtattcctt     2460
ggacacataa ggtgggaaac tttacggggc tttattcttc tacggtacct tgctttaatc    2520
ctaaatggca aactccttct tttcctgaca ttcatttgca ggaggacatt gttgatagat    2580
gcaagcaatt tgtgggggccc cttacagtaa atgaaaacag gagactaaaa ttaattatgc    2640
ctgctaggtt ttatcccaat gttactaaat atttgccctt agataaaggg atcaaaccgt    2700
attatccaga gtatgtagtt aatcattact ttcagacgcg acattattta cacactcttt    2760
ggaaggcggg gatcttatat aaaagagagt ccacacgtag cgcctcattt tgcgggtcac    2820
catattcttg ggaacaagat ctacagcatg ggaggttggt cttccaaacc tcgaaaaggc    2880
atggggacaa atctttctgt ccccaatccc ctgggattct tccccgatca tcagttggac    2940
cctgcattca aagccaactc agaaaatcca gattgggacc tcaacccgca caaggacaac    3000
tggccggacg ccaacaaggt gggagtggga gcattcgggc cagggttcac ccctcccccat   3060 gggggactgt tggggtggag ccctcaagct cagggcctac tcacaactgt gccagcagct    3120
cctcctcctg cctccaccaa tcggcagtca ggaaggcagc ctactccctt atctccacct    3180
ctaagggaca ctcatcctca ggccatgcag tggaa                               3215

<210> SEQ ID NO 2
<211> LENGTH: 3215
<212> TYPE: DNA
<213> ORGANISM: Hepatitis B virus
<220> FEATURE:
<223> OTHER INFORMATION: exemplary HBV genotype C1 isolate

<400> SEQUENCE: 2
ctccagcaca ttccaccaag ctctgctaga tcccagagtg aggggcctat accttcctgc     60
tggtggctcc agttccggaa cagtaaaccc tgttccgact actgcctctc ccatatcgtc    120
aatcttctcg aggactgggg accctgcacc gaatatggag agcaccacat caggattcct    180
```

```
aggacccctg ctcgtgttac aggcggggtt tttcttgttg acaagaatcc tcacaatacc      240
acagagtcta gactcgtggt ggacttctct caatttctca gggggagcac ccacgtgtcc      300
tggccaaaat ttgcagtccc caacctccaa tcactcacca acctcttgtc ctccaatttg      360
tcctggttat cgctggatgt gtctgcggcg ttttatcatc ttcctcttca tcctgctgct      420
atgcctcatc ttcttgttgg ttcttctgga ctaccaaggt atgttgcccg tttgtcctct      480
acttccagga acatcaacta ccagcacggg accatgcaag acctgcacga ttcctgctca      540
aggaacctct atgtttccct cttgttgctg tacaaaacct tcggacggaa attgcacttg      600
tattcccatc ccatcatctt gggctttcgc aagattccta tgggagtggg cctcagtccg      660
tttctcctgg ctcagtttac tagtgccatt tgttcagtgg ttcgtagggc tttcccccac      720
tgtttggctt tcagttatat ggatgatgtg gtattggggg ccaagtctgt acaacatctt      780
gaatcccttt ataccgctat taccaatttt cttgtgtctt tgggtataca tttaaaccct      840
aataaaacca aacgttgggg ctactccctt aacttcatgg gatatgtaat tggaagttgg      900
ggtaccttgc cacaggaaca tattgtacaa aaaatcaaac aatgttttcg aaaacttcct      960
ataaatagac ctattgattg gaaagtatgt caaagaattg tgggtctttt gggttttgcc     1020
gctcccttta cacaatgtgg ttacccagca ttaatgcctt tatatgcatg tatacaagct     1080
aaacaggctt tcactttctc gccaacttac aaggcctttc tgtataaaca atatctgaac     1140
ctttaccccg ttgctcggca acggtcaggt ctttgccaag tgtttgctga cgcaaccccc     1200
actggttggg gcttggccat gggccatcag cgcatgcgtg gaacctttgt ggctcctctg     1260
ccgatccata ctgcggaact cctagcagct tgttttgctc gcagccggtc tggagcaaac     1320
cttatcggca ccgacaactc tgttgtcctc tctcggaaat acacctcttt tccatggctg     1380
ctaggctgtg ctgccaactg gatcctgcgc gggacgtcct tgtctacgt  cccgtcggcg     1440 ctgaatcccg cggacgaccc gtctcggggt cgtttgggac tctaccgtcc ccttctccgt     1500
ctgccgttcc ggccgaccac ggggcgcacc tctctttacg cggactcccc gtctgtgcct     1560
tctcatctgc cggaccgtgt gcacttcgct tcacctctgc acgtcgcatg gagaccaccg     1620
tgaacgcccg ccaggtcttg cctaaggtct tacataagag gactcttgga ctctcagcaa     1680
tgtcaacgac cgaccttgag gcatacttca aagactgtgt atttaaggac tgggaggagt     1740
tgggggagga gattaggtta atgatctttg tactgggagg ctgtaggcat aaattggtct     1800
gttcaccagc accatgcaac ttttttcacct ctgcctaatc atctcatgtt catgttccac     1860
tgttcaagcc tccaagctgt gccttgggtg gctttggggc atggacattg acccgtataa     1920
agaatttgga gcttctgtgg agttactctc ttttttgcct tctgacttt  ttccttctat     1980 tcgtgatctc ctcgacaccg cctctgctct gtatcggagg ccttagagt  ctccggaaca     2040 ttgttcacct caccatacag cactaaggca agctattctg tgttggggtg agttgatgaa     2100
tctggccacc tgggtgggaa gtaatttgga agacccggca tccagggaat tagtagtaag     2160
ctatgtcaat gttaatatgg gcctaaaaat cagacaacta ttgtggtttc acatttcctg     2220
tcttactttt ggaagagaaa ctgttcttga gtatttggtg tcttttggag tgtggattcg     2280
cactcctccc gcttacagac caccaaatgc ccctatctta tcaacacttc cggaaactac     2340
tgttgttaga cgacgaggca ggtcccctag aagaagaact ccctcgcctc gcagacgaag     2400
gtctcaatcg ccgcgtcgca gaagatctca gtctcgggaa tctcaatgtt agtatcccct     2460
ggactcataa ggtgggaaac tttactgggc tttattcttc tactgtacct gtctttaatc     2520
ctgaatggca aactccctct tttcctcaca ttcatttgaa agaggatatt atcaatagat     2580
```

```
gtcaacaata tgtgggccct cttacagtta acgaaaaaag gagattaaaa ttgatcatgc    2640
ctgctaggtt ctatcctaac cttactaaat atttgccctt agataaaggc atcaaacctt    2700
attatcctga acatatagtt aatcattact tccaaactag gcattattta catactctgt    2760
ggaaggctgg tattttatat aagagagaaa ctactcgcag cgcctcattt tgtgggtcac    2820
catattcttg ggaacaagag ctacagcatg ggaggttggt cttccaaacc tcgacaaggc    2880
atggggacga atctttccgt tcccaatcct ctgggattct ttcccggtca ccagttggac    2940
ccgacattcg gagccaattc aaacaatcca gattgggact caacccccaa caaggatcaa    3000
tggccagcgg caaaccaggt aggagtggga tcattcgggc cggggttcac tccaccacac    3060
ggcaatcttt tggggtggag ccctcaggct cagggcatat tgacaacagt accagcagcg    3120
cctcctcctg cctccaccaa tcggcagtca ggaagaaagc ctactcccat ctctccacct    3180
ctaagagaca gtcatcctca ggccatgcaa tggaa                              3215

<210> SEQ ID NO 3
<211> LENGTH: 3215
<212> TYPE: DNA
<213> ORGANISM: Hepatitis B virus
<220> FEATURE:
<223> OTHER INFORMATION: exemplary HBV genotype C2 isolate

<400> SEQUENCE: 3
ctccagcaca ttccaccaag ctctgctaga tcccagagtg aggggcctat accttcctgc      60
tggtggctcc agttccggaa cagtaaaccc tgttccgact actgcctctc ccatatcgtc     120
aatcttctcg aggactgggg accctgcacc gaatatggag agcaccacat caggattcct     180
aggacccctg ctcgtgttac aggcggggtt tttcttgttg acaagaatcc tcacaatacc     240
acagagtcta gactcgtggt ggacttctct caattttcta gggggagcac ccacgtgtcc     300
tggccaaaat tgcagtccca caacctccaa tcactcacca acctcttgtc ctccaatttg     360
tcctggttat cgctggatgt gtctgcggcg ttttatcatc ttcctcttca tcctgctgct     420
atgcctcatc ttcttgttgg ttcttctgga ctaccaaggt atgttgcccg tttgtcctct     480
acttccagga acatcaacta ccagcacggg accatgcaag acctgcacga ttcctgctca     540
aggaacctct atgtttccct cttgttgctg tacaaaacct tcggacggaa attgcacttg     600
tattcccatc ccatcatctt gggctttcgc aagattccta tgggagtggg cctcagtccg     660
tttctcctgg ctcagtttac tagtgccatt tgttcagtgg ttcgtagggc tttcccccac     720
tgtttggctt tcagttatat ggatgatgtg gtattggggg ccaagtctgt acaacatctt     780
gaatcccttt ataccgctat taccaatttt cttgtgtctt tgggtataca tttaaaccct     840
aataaaacca aacgttgggg ctactccctt aacttcatgg gatatgtaat tggaagttgg     900
ggtaccttgc cacaggaaca tattgtacaa aaaatcaaac aatgttttcg aaaacttcct     960
ataaatagac ctattgattg gaaagtatgt caaagaattg tgggtctttt gggttttgcc    1020
gctccctttA cacaatgtgg ttacccagca ttaatgcctt tatatgcatg tatacaagct    1080
aaacaggctt tcactttctc gccaacttac aaggcctttc tgtataaaca atatctgaac    1140
ctttaccccg ttgctcggca acggtcaggt ctttgccaag tgtttgctga cgcaaccccc    1200
actggttggg gcttggccat gggccatcag cgcatgcgtg gaacctttgt ggctcctctg    1260
ccgatccata ctgcggaact cctagcagct tgttttgctc gcagccggtc tggagcaaac    1320
cttatcggca ccgacaactc tgttgtcctc tctcggaaat acacctcttt tccatggctg    1380
```

```
ctaggctgtg ctgccaactg gatcctgcgc gggacgtcct ttgtctacgt cccgtcggcg   1440
ctgaatcccg cggacgaccc gtctcggggt cgtttgggac tctaccgtcc ccttctccgt   1500
ctgccgttcc ggccgaccac ggggcgcacc tctctttacg cggactcccc gtctgtgcct   1560
tctcatctgc cggaccgtgt gcacttcgct tcacctctgc acgtcgcatg gagaccaccg   1620
tgaacgcccg ccaggtcttg cctaaggtct tacataagag gactcttgga ctctcagcaa   1680
tgtcaacgac cgaccttgag gcatacttca aagactgtgt atttaaggac tgggaggagt   1740
tgggggagga gattaggtta atgatctttg tactgggagg ctgtaggcat aaattggtct   1800
gttcaccagc accatgcaac ttttttcacct ctgcctaatc atctcatgtt catgttccac   1860
tgttcaagcc tccaagctgt gccttgggtg gctttgggc atggacattg acccgtataa   1920
agaatttgga gcttctgtgg agttactctc ttttttgcct tctgactttt ttccttctat   1980
tcgtgatctc ctcgacaccg cctctgctct gtatcgggag gccttagagt ctccggaaca   2040
ttgttcacct caccatacag cactaaggca agctattctg tgttggggtg agttgatgaa   2100
tctggccacc tgggtgggaa gtaatttgga agacccggca tccagggaat tagtagtaag   2160
ctatgtcaat gttaatatgg gcctaaaaat cagacaacta ttgtggtttc acatttcctg   2220
tcttactttt ggaagagaaa ctgttcttga gtatttggtg tcttttggag tgtggattcg   2280
cactcctccc gcttacagac caccaaatgc ccctatctta tcaacacttc cggaaactac   2340
tgttgttaga cgacgaggca ggtcccctag aagaagaact ccctcgcctc gcagacgaag   2400
gtctcaatcg ccgcgtcgca gaagatctca gtctcgggaa tctcaatgtt agtatccctt   2460
ggactcataa ggtgggaaac tttactgggc tttattcttc tactgtacct gtctttaatc   2520
ctgaatggca aactccctct tttcctcaca ttcatttgaa agaggatatt atcaatagat   2580
gtcaacaata tgtgggccct cttacagtta acgaaaaaag gagattaaaa ttgatcatgc   2640
ctgctaggtt ctatcctaac cttactaaat atttgcccct agataaaggc atcaaacctt   2700
attatcctga acatatagtt aatcattact tccaaactag gcattattta catactctgt   2760
ggaaggctgg tattttatat aagagagaaa ctactcgcag cgcctcattt tgtgggtcac   2820
catattcttg ggaacaagag ctacagcatg ggaggttggt cttccaaacc tcgacaaggc   2880
atggggacga atcttttccgt tcccaatcct ctgggattct ttcccggtca ccagttggac   2940
ccgacattcg gagccaattc aaacaatcca gattgggact tcaaccccaa caaggatcaa   3000
tggccagcgg caaaccaggt aggagtggga tcattcgggc cggggttcac tccaccacac   3060
ggcaatcttt tggggtggag ccctcaggct cagggcatat tgacaacagt accagcagcg   3120
cctcctcctg cctccaccaa tcggcagtca ggaagaaagc ctactcccat ctctccacct   3180
ctaagagaca gtcatcctca ggccatgcaa tggaa                              3215
```

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence:long
      distance semi-nested amplification PCR sense primer P1

<400> SEQUENCE: 4
tttttcacct ctgcctaatc a                                               21

<210> SEQ ID NO 5
<211> LENGTH: 22
<212> TYPE: DNA

```
<213> ORGANISM: Artificial Sequence
<220> FEATURE:
<223> OTHER INFORMATION: Description of Artificial Sequence:long
      distance semi-nested amplification PCR antisense primer P2

<400> SEQUENCE: 5
ccctagaaaa ttgagagaag tc                                          22

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence:long
      distance semi-nested amplification PCR antisense primer and
      Fragment A sequencing primer P3

<400> SEQUENCE: 6
ccactgcatg gcctgaggat g                                           21

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence:long
      distance semi-nested amplification PCR sense primer P4

<400> SEQUENCE: 7
gcctcatttt gtgggtcacc ata                                         23

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence:long
      distance semi-nested amplification PCR antisense primer P5

<400> SEQUENCE: 8
ttctttgaca tactttcca                                              19

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence:long
      distance semi-nested amplification PCR sense primer and
      Fragment B sequencing primer P6

<400> SEQUENCE: 9
ttggggtgga gccctcaggc t                                           21

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence:long
      distance semi-nested amplification PCR sense primer and
      Fragment B sequencing primer P7

<400> SEQUENCE: 10
ttggccaaaa ttcgcagtc                                              19

<210> SEQ ID NO 11
```

-continued

```
<211> LENGTH: 20
<212> TYPE: DNA
<213> ORGANISM: Artificial Sequence
<220> FEATURE:
<223> OTHER INFORMATION: Description of Artificial Sequence:long
      distance semi-nested amplification PCR sense primer and
      Fragment C sequencing primer P8

<400> SEQUENCE: 11
ccccactgtt tggctttcag                                              20

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence:long
      distance semi-nested amplification PCR antisense primer and
      Fragment C sequencing primer P9

<400> SEQUENCE: 12
gttgataaga tagggcatt tggtgg                                        26

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence:Fragment A
      sense sequencing primer S1

<400> SEQUENCE: 13
ctccggaaca ttgttcacct                                              20

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence:Fragment A
      sense sequencing primer S2

<400> SEQUENCE: 14
aaggtgggaa actttactgg gc                                           22

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence:Fragment C
      sense sequencing primer S3

<400> SEQUENCE: 15
gctgacgcaa cccccactgg                                              20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence:Fragment C
      sense sequencing primer S4

<400> SEQUENCE: 16
tcgcatggag accaccgtga                                              20
```

```
<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence:Fragment C
      antisense sequencing primer S5

<400> SEQUENCE: 17
ggcaaaaacg agagtaactc                                              20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence:Fragment C
      antisense sequencing primer S6

<400> SEQUENCE: 18
gggtcgtccg cgggattcag                                              20

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence:Fragment B
      antisense sequencing primer S7

<400> SEQUENCE: 19
gacatacttt ccaatcaata gg                                           22

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence:Fragment B
      antisense sequencing primer S8

<400> SEQUENCE: 20
gaagatgagg catagcagca gg                                           22

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence:Fragment A
      antisense sequencing primer S9

<400> SEQUENCE: 21
catgctgtag ctcttgttcc                                              20
```

US 7,871,780 B2

GENOMIC MARKERS OF HEPATITIS B VIRUS ASSOCIATED WITH HEPATOCELLULAR CARCINOMA

CROSS-REFERENCE TO RELATED PATENT APPLICATIONS

The present patent application is a divisional of U.S. patent application Ser. No. 11/019,426, filed Dec. 20, 2004, now U.S. Pat. No. 7,439,020, issued on Oct. 21, 2008, which is a continuation-in-part of U.S. patent application Ser. No. 10/937,987, filed Sep. 10, 2004, now abandoned, the disclosure of each is herein incorporated by reference in its entirety.

BACKGROUND OF THE INVENTION

Hepatitis B virus (HBV) infects over 300 million people worldwide. For those individuals with high levels of viral replication, chronic active hepatitis with progression to cirrhosis, liver failure and hepatocellular carcinoma (HCC) is common.

The natural progression of chronic HBV infection over a 10 to 20 year period leads to cirrhosis in 20-to-50% of patients and progression of HBV infection to hepatocellular carcinoma has been well documented. There have been no studies that have determined sub-populations of hepatitis B virus that are most likely to cause hepatocellular carcinoma, thus to date all hepatitis B virus have been considered of equal risk of hepatocarcarcinogesis.

It is important to note that the survival for patients diagnosed with hepatocellular carcinoma is only 0.9 to 12.8 months from initial diagnosis (Takahashi et al., *American Journal of Gastroenterology* 88:240-243 (1993)). Treatment of hepatocellular carcinoma with chemotherapeutic agents has not proven effective and only 10% of patients will benefit from surgery due to extensive tumor invasion of the liver (Trinchet et al., *Presse Medicine* 23:831-833 (1994)). Given the aggressive nature of primary hepatocellular carcinoma, the only viable treatment alternative to surgery is liver transplantation (Pichlmayr et al., *Hepatology* 20:33 S-40S (1994)).

BRIEF SUMMARY OF THE INVENTION

The present invention provides for methods of determining a pre-disposition of an individual infected with hepatitis B virus (HBV) to develop hepatocellular carcinoma (HCC). In some embodiments, the methods comprise:

(a) determining nucleotides in the genome of HBV isolated from the individual at positions corresponding to nucleotides 31, 53, 312, 799, 961, 1165, 1499, 1613, 1762, 1764, 1899, 2170, 2441, 2525, and/or 2712 of SEQ ID NO:1; and (b) comparing the determined nucleotides to nucleotides associated with a pre-disposition to cause HCC, wherein the nucleotides associated with a pre-disposition to cause HCC comprise: 31C, 53C, 312C, 799G, 961G, 1165T, 1499G, 1613A, 1762T, 1764A, 1899A, 2170C, 2170G, 2441C, 2525C, 2712C, 2712A, and/or 2712G.

In some embodiments, the methods comprise:

(a) determining nucleotides in the genome of a genotype B HBV isolated from the individual at positions corresponding to nucleotides 1165, 1762, 1764, 2525 or 2712 of SEQ ID NO:1; and (b) comparing the determined nucleotides to nucleotides associated with a pre-disposition to cause HCC, wherein the nucleotides associated with a pre-disposition to cause HCC comprise: 1165T, 1762T, 1764A, 2525C, 2712C, 2712A, or 2712G.

In some embodiments, the methods comprise:

(a) determining nucleotides in the genome of a genotype B HBV isolated from the individual at positions corresponding to nucleotides 1165, 1762, 1764, 2525 and 2712 of SEQ ID NO:1; and (b) comparing the determined nucleotides to nucleotides associated with a pre-disposition to cause HCC, wherein the nucleotides associated with a pre-disposition to cause HCC in genotype B comprise:

1762T and 1764A and 2712A; or
1762T and 1764A and 2712C; or
1762T and 1764A and 2712G; or
1762T and 1764A and 2712T and 2525C; or
1762A and 1764G and 1165T.

In some embodiments, the method comprises determining the genotype of the HBV from the individual.

In some embodiments, the determining step comprises nucleotide sequencing the HBV genome flanking the nucleotides at positions corresponding to nucleotides 1165, 1762, 1764, 2525 and 2712 of SEQ ID NO:1.

In some embodiments, the determining step comprises amplifying at least a portion of the HBV genome to produce one or more amplification products comprising the nucleotides at the positions corresponding to nucleotides 1165, 1762, 1764, 2525 and 2712 of SEQ ID NO:1. In some embodiments, the method comprises contacting the one or more amplification products with one or more probes that hybridize to HCC-associated nucleotides:

1762T and 1764A and 2712A; or
1762T and 1764A and 2712C or;
1762T and 1764A and 2712G; or
1762T and 1764A and 2712T and 2525C; or
1762A and 1764G and 1165T;

under conditions to allow for hybridization of a probe to an amplification product only if the amplification product comprises a complementary nucleotide at the position of the HCC-associated nucleotide. In some embodiments, the hybridization is performed as a line probe assay.

In some embodiments, the method comprises:

(a) determining nucleotides in the genome of a genotype C HBV isolated from the individual at positions corresponding to nucleotides 31, 53, 312, 799, 961, 1499, 1613, 1899, 2170, or 2441; and (b) comparing the determined nucleotides to nucleotides associated with a pre-disposition to cause HCC, wherein the nucleotides associated with a pre-disposition to cause HCC comprise: 31C, 53C, 312C, 799G, 961G, 1499G, 1613A, 1899A, 2170C, 2170G, or 2441C.

In some embodiments, the method comprises a) determining the subtype of a genotype C HBV from the individual, wherein:

subtype C1 comprises nucleotides 2733A, 1856C, 1009T and 2892T,
subtype C2 comprises nucleotides 2733C, 1856T, 1009T and 2892T, and
subtype C3 comprises nucleotides 2733C, 1856C, 1009C and 2892T;

b1) if the HBV is genotype C1, determining the nucleotides at positions corresponding to nucleotides 31, 53 and 1499 of SEQ ID NO:1; or b2) if the HBV is genotype C2, determining the nucleotides at positions corresponding to nucleotides 799, 2441 and 2170 of SEQ ID NO:1; and b3) if the HBV is genotype C3, determining the nucleotides at positions corresponding to nucleotides 312, 961, 1613, 1899 of SEQ ID NO:1; and c) comparing the determined nucleotides to nucleotides at the positions associated with a pre-disposition to cause HCC, wherein the nucleotides associated with a pre-disposition to cause HCC in subtype C1 comprise:
31C; and/or
53C; and/or
1499G; and
the nucleotides associated with a pre-disposition to cause HCC in subtype C2 comprise:
2170C; and/or
2170G; and/or
2441C; and/or
799G; and
the nucleotides associated with a pre-disposition to cause HCC in subtype C3 comprise:
312C; and/or
961G; and/or
1613A; and/or
1899A In some embodiments, the determining step comprises nucleotide sequencing the HBV genome flanking the nucleotides at positions corresponding to nucleotides 31, 53, and 1499 of SEQ ID NO:1. In some embodiments, the determining step comprises nucleotide sequencing the HBV genome flanking the nucleotides at positions corresponding to nucleotides 799, 2441, and 2170 of SEQ ID NO:1. In some embodiments, the determining step comprises amplifying at least a portion of the HBV genome to produce one or more amplification products comprising the nucleotides at the positions corresponding to nucleotides 31, 53, and 1499 of SEQ ID NO:1. In some embodiments, the determining step comprises nucleotide sequencing the HBV genome flanking the nucleotides at positions corresponding to nucleotides 312, 961, 1613, and 1899 of SEQ ID NO:1

In some embodiments, the determining step comprises amplifying at least a portion of the HBV genome to produce one or more amplification products comprising the nucleotides at the positions corresponding to nucleotides 799, 2441, and 2170 of SEQ ID NO:1. In some embodiments, the determining step comprises amplifying at least a portion of the HBV genome to produce one or more amplification products comprising the nucleotides at the positions corresponding to nucleotides 312, 961, 1613, and 1899 of SEQ ID NO:1.

In some embodiments, the method comprises contacting the one or more amplification products with one or more probes that hybridize to HCC-associated nucleotides:
31C; and/or
53C; and/or
1499G;

under conditions to allow for hybridization of a probe to an amplification product only if the amplification product comprises a complementary nucleotide at the position of the HCC-associated nucleotide.

In some embodiments, the hybridization is performed as a line probe assay.

In some embodiments, the method comprises contacting the one or more amplification products with probes that hybridize to HCC-associated nucleotides:
2170G; and/or
2441C; and/or
799G;

under conditions to allow for hybridization of the probes to the amplification product only if the amplification product comprises a complementary nucleotide at the position of the HCC-associated nucleotide. In some embodiments, the hybridization is performed as a line assay.

In some embodiments, the method comprises contacting the one or more amplification products with probes that hybridize to HCC-associated nucleotides:
312C; and/or
961G; and/or
1613A; and/or
1899A;

under conditions to allow for hybridization of the probes to the amplification product only if the amplification product comprises a complementary nucleotide at the position of the HCC-associated nucleotide. In some embodiments, the hybridization is performed as a line assay.

In some embodiments, the method further comprises determining the genotype of the HBV from the individual.

In some embodiments, the method comprises:
determining the genotype of the HBV, wherein genotype B comprises 2733C, 1856C, 1009T and 2892T, genotype C1 comprises 2733A, 1856C, 1099T and 2892T, genotype C2 comprises 2733C, 1856T, 1009T and 2892T and genotype C3 comprises 2733C, 1856C, 1009C and 2892T;

determining nucleotides 1165, 1762, 1764, 2525 and 2712 of the HBV genome if the HBV is genotype B; and/or determining nucleotides 31 and/or 53 and/or 1499 of the HBV genome if the HBV is C1; and/or determining nucleotides 2170 and/or 2441 and/or 799 of the HBV genome if the HBV is C2; and/or determining nucleotides 312 and/or 961 and/or 1613 and/or 1899 of the HBV genome if the HBV is C3; and comparing the determined nucleotides to nucleotides associated with a pre-disposition to cause HCC, wherein nucleotides associated with a pre-disposition to cause HCC in genotype B comprise:
1762T and 1764A and 2712A; or
1762T and 1764A and 2712C or;
1762T and 1764A and 2712G; or
1762T and 1764A and 2712T and 2525C; or
1762A and 1764G and 1165T;

wherein nucleotides associated with a pre-disposition to cause HCC in genotype C1 comprise:
31C; and/or
53C; and/or
1499G; and wherein nucleotides associated with a pre-disposition to cause HCC in genotype C2 comprise:
2170C; and/or
2170G; and/or
2441C; and/or
799G;

wherein nucleotides associated with a pre-disposition to cause HCC in genotype C3 comprise:
312C; and/or
961G; and/or
1613A; and/or
1899A;

thereby determining the pre-disposition of the individual to develop HCC.

The present invention also provides kits for detecting HBV isolates that are associated with the development hepatocellular carcinoma (HCC).

In some embodiments, the kits comprise:

one or more probe which, when contacted to an HBV genome, selectively hybridizes to the genome if the genome comprises at least one of the following nucleotides: 31C, 53C, 312C, 799G, 961G, 1165T, 1499G, 1613A, 1762T, 1762A, 1764A, 1764G, 1899A, 2441C, 2170C, 2170G, 2712A, 2712C, 2712G; or 2525C.

In some embodiments, the probe is linked to a solid support.

In some embodiments, the probe selectively hybridizes to:
1762T and 1764A and 2712A; and/or
1762T and 1764A and 2712C; and/or;
1762T and 1764A and 2712G; and/or
1762T and 1764A and 2712T and 2525C; and/or
1762A and 1764G and 1165T.

In some embodiments, the probe selectively hybridizes to:
31C; and/or
53C; and/or
1499G.

In some embodiments, the probe selectively hybridizes to:
2170C; and/or
2170G; and/or
2441C; and/or
799G.

In some embodiments, the probe selectively hybridizes to:
312C; and/or
961G; and/or
1613A; and/or
1899A.

In some embodiments, the kits further comprise primers for amplification of at least a portion of the HBV genome.

The present invention also provides a computer readable medium for determining whether an HBV sequence is likely to result in the development of HCC. In some embodiments, the computer readable form comprises:
a) code for receiving information describing: nucleotides at positions corresponding to nucleotides 31, 53, 312, 799, 961, 1165, 1499, 1613, 1762, 1764, 1899, 2170, 2441, 2525, or 2712 of SEQ ID NO:1;
b) code for comparing the nucleotides received in a) to nucleotides associated with a pre-disposition to cause HCC; and
c) code for providing a determination of the pre-disposition of the HBV to cause HCC, wherein nucleotides associated with a pre-disposition to cause HCC comprise: 31C, 53C, 312C, 799G, 961G, 1165T, 1499G, 1613A, 1762T, 1764A, 1899A, 2170C, 2170G, 2441C, 2525C, 2712C, 2712A, or 2712G.

Definitions

A probe "selectively hybridizes" to a viral genome comprising a particular nucleotide when the probe hybridizes to the genome when the particular nucleotide (at the specified position) is present, but does not hybridize if the nucleotide at the specified position is different or absent. Conditions to allow for hybridization of a probe to a particular DNA molecule only if a complementary nucleotide is present in a particular target DNA are generally "stringent hybridization conditions."

The phrase "stringent hybridization conditions" refers to conditions under which a probe will hybridize to its target subsequence, typically in a complex mixture of nucleic acid, but to no other sequences, or at least to no other sequences at which a particular position is anything but one particular nucleotide. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions for Southern hybridization are generally those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective hybridization, a positive signal is at least two times background, optionally 10 times background hybridization, i.e., hybridization to another nucleotide sequence with a different nucleotide at the position of interest. Exemplary stringent hybridization conditions can be as follows: 50% formamide, 5×SSC, and 1% SDS, incubating at 42° C., or 5×SSC, 1% SDS, incubating at 65° C., with wash in 0.2×SSC, and 0.1% SDS at 65° C. Such washes can be performed for 5, 15, 30, 60, 120, or more minutes.

"Determining nucleotides in the genome of HBV at positions corresponding to" particular nucleotides of a reference sequence (e.g., SEQ ID NO:1) refers to identifying a position in an isolated HBV genome that occurs in a position that is the equivalent of the particular position in the reference sequence. The variants identified in the present invention are not limited to predicting sequence pre-disposition of variants of SEQ ID NO:1, but instead apply to any HBV strain carrying particular corresponding nucleotides. Thus, when the genome of an HBV isolate differs from SEQ ID NO:1 (e.g., by changes in nucleotides or addition or deletion of nucleotides), it may be that a particular nucleotide associated with the development of HCC will not be in exactly the same position as it is in SEQ ID NO:1. For example, the nucleotide corresponding to nucleotide 31C of SEQ ID NO:1 may occur at position 32 of a particular HBV strain due to a one nucleotide insertion at an earlier position in the strain's genome. Nevertheless, position 32 of the HBV strain would correspond to position 31 of SEQ ID NO:1, which can be readily illustrated in an alignment of the two sequences. As described herein, the corresponding nucleotide in the genome of an HBV isolate can be determined using an alignment algorithm such as BLAST.

BRIEF DESCRIPTION OF THE DRAWINGS

FIG. 1 illustrates the locations of various primers used for amplification of HBV and the resulting amplified fragments relative to the HBV genome, represented as a line at the bottom of the figure.

FIGS. 2A and 2B illustrate the genome (SEQ ID NO:1) of an exemplary HBV genotype B isolate comprising highlighted nucleotides associated with the development of HCC.

FIGS. 3A and 3B illustrate the genome (SEQ ID NO:2) of an exemplary HBV genotype C1 isolate comprising highlighted nucleotides associated with the development of HCC.

FIGS. 4A and 4B illustrate the genome (SEQ ID NO:3) of an exemplary HBV genotype C2 isolate comprising highlighted nucleotides associated with the development of HCC.

DETAILED DESCRIPTION OF THE INVENTION

I. Introduction

The present invention is based on the discovery that certain sequence variants of HBV are associated with the development of hepatocellular carcinoma (HCC) in individuals infected with HBV. Specifically, the presence of the following nucleotides in an HBV genome is associated with the development of HCC: 31C, 53C, 312C, 799G, 961G, 1165T, 1499G, 1613A, 1762T, 1764A, 1899A, 2170C, 2170G, 2441C, 2525C, 2712C, 2712A, or 2712G. Accordingly, the invention provides for methods of determining whether an individual infected with HBV has a predisposition for HCC by detecting the nucleotide sequence of the HBV variant infecting the individual. The method also provides for kits comprising reagents to detect any of the specific variants associated with HCC and computer readable forms for applying the methods of the invention.

II. Detecting HBV Variants Associated with HCC

Any number of methods may be used to determine the nucleotides at the positions corresponding to nucleotides at positions 31, 53, 312, 799, 961, 1165, 1499, 1613, 1762, 1764, 1899, 2170, 2441, 2525, and/or 2712 of SEQ ID NO:1 and/or other positions as described herein.

In some embodiments, nucleotide sequencing is used to determine the nucleotides at particular positions of the HBV genome. Without intending to limit the invention, examples of nucleotide sequencing include chain termination sequencing. See, e.g., Sanger et al. *Proc. Nat. Acad. Sci. USA* 74:5463-5467 (1977); Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)). Sequencing may be performed following amplification of the HBV genome or a fragment thereof. Direct sequencing of PCR generated amplicons by selectively incorporating boronated nuclease resistant nucleotides into the amplicons during PCR and digestion of the amplicons with a nuclease to produce sized template fragments may also be performed (Porter et al., *Nucleic Acids Research* 25(8):1611-1617 (1997)). Alternatively, microfluidic techniques such as those described in U.S. Patent Publication No. 2003/0215862 may be used. See also U.S. Patent Publication No. 2003/0152996 describing alternate sequencing methods.

Specific probes that bind to nucleotides at particular positions in the HBV genome may also be used to detect nucleotides in the HBV genome. Probes that detect the particular nucleotides associated with HCC may be used in a reverse hybridization assay format using immobilized oligonucleotide probes present at distinct locations on a solid support. More particularly, the Line Probe Assay (LiPA) may be used. The LiPA is a reverse hybridization assay using oligonucleotide probes immobilized as parallel lines on a solid support strip. See, e.g., PCT Publication No. WO 94/12670. In this assay, specific oligonucleotides may be immobilized at known locations on membrane strips and hybridized under strictly controlled conditions with the labeled PCR product. Different probes may be designed such that each probe on the strip comprises an HBV nucleotide sequence, or complement thereof, but contains a different nucleotide at a particular position. Amplifying an HBV genome, or fragment thereof, and hybridizing the amplification product to one or more probes specific for a particular variant will result in complete or at least preferential hybridization of one of the probes to the product, thereby indicating which nucleotide at the particular position is contained in the amplified genome. Hybridization conditions using this assay are generally set at a high stringency such that only one probe binds to the amplification product. Exemplary conditions may include, e.g., standard hybridization and washing conditions (e.g., 1×SSC buffer containing 0.1% sodium dodecyl sulfate at 62° C.).

Amplification of HBV

The HBV genome or a portion thereof may be amplified before the nucleotides at positions associated with HCC are determined. An "amplification" refers to any chemical, including enzymatic, reaction that results in increased copies of a template nucleic acid sequence. Amplification reactions include polymerase chain reaction (PCR) and ligase chain reaction (LCR) (see U.S. Pat. Nos. 4,683,195 and 4,683,202; *PCR Protocols: A Guide to Methods and Applications* (Innis et al., eds, 1990)), strand displacement amplification (SDA) (Walker, et al. *Nucleic Acids Res.* 20(7): 1691-6 (1992); Walker PCR *Methods Appl* 3(1):1-6 (1993)), transcription-mediated amplification (Phyffer, et al., *J. Clin. Microbiol.* 34:834-841 (1996); Vuorinen, et al., *J. Clin. Microbiol.* 33:1856-1859 (1995)), nucleic acid sequence-based amplification (NASBA) (Compton, *Nature* 350(6313):91-2 (1991), rolling circle amplification (RCA) (Lisby, *Mol. Biotechnol.* 12(1):75-99 (1999)); Hatch et al., *Genet. Anal.* 15(2):35-40 (1999)) and branched DNA signal amplification (bDNA) (see, e.g., Iqbal et al., *Mol. Cell Probes* 13(4):315-320 (1999)).

Amplified portions of the HBV genome (optionally labeled) may be hybridized to DNA comprising one or more HCC-associated nucleotides, or a complement thereof, thereby allowing for determination of the identity of nucleotides at a nucleotide position of interest. Alternatively, the probes may detect non-HCC-associated nucleotides, thereby allowing for detection of HCC-associated HBV variants by detecting a lack of hybridization.

In some embodiments, the amplified fragment of the genome will comprise more than one HCC-associated nucleotide. Thus, in some embodiments, the fragment will comprise any combination of positions corresponding to nucleotides at positions 31, 53, 312, 799, 961, 1165, 1499, 1613, 1762, 1764, 1899, 2170, 2441, 2525, and/or 2712 of SEQ ID NO:1. In some embodiments, the fragment will comprise positions corresponding to nucleotides 1165, 1762, 1764, 2525 and 2712 of SEQ ID NO:1. In some embodiments, the fragment will comprise positions corresponding to nucleotides 31, 53, 312, 799, 961, 1499, 1613, 1899, 2170, and 2441 of SEQ ID NO:1.

In some cases, more than one fragment of HBV is amplified. In these cases, the sum of all fragments amplified may comprise any combination of positions corresponding to nucleotides at positions 31, 53, 312, 799, 961, 1165, 1499, 1613, 1762, 1764, 1899, 2170, 2441, 2525, and/or 2712 of SEQ ID NO:1. For example, one fragment may comprise positions 31, 53, 312, 799, 961, 1165, 1499, 1613, 1762, 1764 and a second fragment may comprise positions 1899, 2170, 2441, 2525, or 2712. In some embodiments, the sum of all amplified fragments will comprise positions corresponding to nucleotides 1165, 1762, 1764, 2525 and 2712 an SEQ ID NO:1. In some embodiments, the sum of all amplified fragments will comprise positions corresponding to nucleotides 31, 53, 312, 799, 961, 1499, 1613, 1899, 2170, and 2441.

In some embodiments, amplification and detection methods are used in combination, and sometimes in the same reaction vessel, to detect HBV polynucleotides using detectably-labeled probes that distinguish between HCC-associated nucleotides and nucleotides not associated with HCC. Binding of a probe to its complementary hybridization sequence allows the user to quantify the accumulation of a particular sequence without necessarily removing the contents from the reaction vessel. In general, any type of label that allows for the detection and differentiation of different probes can be used according to the methods of the invention.

Accumulation of amplified product can be quantified by any method known to those in the art. For instance, fluorescence from a probe can be detected by measurement of light at a particular frequency. Similarly, the accumulation of various chemical products created via an enzymatic reaction linked to the probe can be measured, for instance, by measuring absorbance of light at a particular wavelength. In other embodiments, amplification reactions can be quantified directly by blotting them onto a solid support and hybridizing with a detectably-labeled nucleic acid probe. Once unbound probe is washed away, the amount of probe can be quantified by measuring radioactivity as is known to those of skill in the art. Other variations of this technique employ the use of chemiluminescence to detect hybridization events.

Measurement of amplification products can be performed after the reaction has been completed or can be measured in "real time" (i.e., as the reaction occurs). If measurement of accumulated amplified product is performed after amplification is complete, then detection reagents (e.g. probes) can be added after the amplification reaction. Alternatively, probes can be added to the reaction prior or during the amplification reaction, thus allowing for measurement of the amplified products either after completion of amplification or in real time. Real time measurements can be particularly useful because they allow for measurement at any given cycle of the reaction and thus provide more information about accumulation of products throughout the reaction. For measurement of amplification product in real time, fluorescent probes are often used.

One amplification assay utilizing a FRET pair to detect an amplification product is the "TaqMan®" assay described in Gelfand et al. U.S. Pat. No. 5,210,015, and Livak et al. U.S. Pat. No. 5,538,848. The probe is a single-stranded oligonucleotide labeled with a FRET pair. In a TaqMan® assay, a DNA polymerase releases single or multiple nucleotides by cleavage of the oligonucleotide probe when it is hybridized to a target strand. That release provides a way to separate the quencher label and the fluorophore label of the FRET pair.

Another type of nucleic acid hybridization probe assay utilizing FRET pairs is described in Tyagi et al. U.S. Pat. No. 5,925,517, which utilizes labeled oligonucleotide probes, which are referred to as "molecular beacons." See Tyagi, S, and Kramer, F. R., *Nature Biotechnology* 14: 303-308 (1996). A molecular beacon probe is an oligonucleotide whose end regions hybridize with one another in the absence of target but are separated if the central portion of the probe hybridizes to its target sequence. The rigidity of the probe-target hybrid precludes the simultaneous existence of both the probe-target hybrid and the intramolecular hybrid formed by the end regions. Consequently, the probe undergoes a conformational change in which the smaller hybrid formed by the end regions disassociates, and the end regions are separated from each other by the rigid probe-target hybrid. For molecular beacon probes, a central target-recognition sequence is flanked by arms that hybridize to one another when the probe is not hybridized to a target strand, forming a "hairpin" structure, in which the target-recognition sequence (which is commonly referred to as the "probe sequence") is in the single-stranded loop of the hairpin structure, and the arm sequences form a double-stranded stem hybrid. When the probe hybridizes to a target, that is, when the target-recognition sequence hybridizes to a complementary target sequence, a relatively rigid helix is formed, causing the stem hybrid to unwind and forcing the arms apart.

One of skill will recognize that a large number of different fluorophores can be used to label probes useful in the invention. Some fluorophores useful in the methods and compositions of the invention include: fluorescein, fluorescein isothiocyanate (FITC), carboxy tetrachloro fluorescein (TET), NHS-fluorescein, 5 and/or 6-carboxy fluorescein (FAM), 5-(or 6-) iodoacetamidofluorescein, 5-{[2(and 3)-5-(Acetylmercapto)-succinyl]amino} fluorescein (SAMSA-fluorescein), and other fluorscein derivatives, rhodamine, Lissamine rhodamine B sulfonyl chloride, Texas red sulfonyl chloride, 5 and/or 6 carboxy rhodamine (ROX) and other rhodamine derivatives, coumarin, 7-amino-methyl-coumarin, 7-Amino-4-methylcoumarin-3-acetic acid (AMCA), and other coumarin derivatives, BODIPY™ fluorophores, Cascade Blue™ fluorophores such as 8-methoxypyrene-1,3,6-trisulfonic acid trisodium salt, Lucifer yellow fluorophores such as 3,6-Disulfonate-4-amino-naphthalimide, phycobiliproteins derivatives, Alexa fluor dyes (available from Molecular Probes, Eugene, Oreg.) and other fluorophores known to those of skill in the art. For a general listing of useful fluorophores, see Hermanson, G. T., BIOCONJUGATE TECHNIQUES (Academic Press, San Diego, 1996). Thus, each probe used in a reaction may fluoresce at a different wavelength and can be individually detected without interference from the other probes. This is useful, for example, if probes that detect different nucleotides at a particular position are used in a reaction. Thus, for example, one wavelength may indicate binding of a probe that detects 31T while a probe comprising a label with a different wavelength will detect 31C.

Preparing HBV from a Test Sample

The presence or amount of HBV nucleic acids in a test sample can be determined by amplifying the target regions within the HBV gene. Thus, any liquid or solid material believed to comprise HBV nucleic acids can be an appropriate sample. Preferred sample tissues include plasma, serum, whole blood, blood cells, lymphatic fluid, cerebral spinal fluid, synovial fluid and others.

As used herein, the term "test sample" refers to any liquid or solid material believed to comprise HBV nucleic acids. A test sample may be obtained from a biological source, such as cells in culture or a tissue sample from an animal, e.g., a human. Sample tissues of the instant invention may include, but are not limited to, plasma, serum, whole blood, blood cells, lymphatic fluid, cerebrospinal fluid, synovial fluid, urine, saliva, and skin or other organs (e.g. liver biopsy material).

Such sample will often be taken from patients suspected of having HBV infection, or having any of the wide spectrum of liver diseases related to HBV infection.

Nucleic acids representing the HBV gene of interest may be extracted from tissue samples. Various commercial nucleic acid purification kits, such as QIAmp 96 Virus BioRobot Kit and Qiagen's BioRobot 9604 are known to the skilled artisan, and used to isolate HBV nucleic acids from samples.

III. Determination of HBV Genotype

The present methods may also involve a determination of the genotype of HBV in an individual. For example, particular nucleotide variants identified herein may have a stronger predisposition to cause HCC if the variants are found in one genotype than in another. In this context, "genotype" refers to the at least 8 genotypes of HBV (genotypes A, B, C, D, E, F, G, and H) deduced from genome comparisons and designated genotypes A to H. See, e.g., Westland C. *Hepatology* 36: 2-8

(2002); Borchani-Chabchoub I, et al., *Microbes Infect* 2: 607-12 (2000); Grandjacques C, et al., *J Hepatol* 33: 430-9 (2000); Kato H, et al., *J Virol Methods* 98: 153-9 (2001); Ashton-Rickardt P G, et al., *J Med Virol* 29: 204-14 (1989). Thus, by detecting nucleotides at particular positions identified to occur only in a specific genotype, one may determine the genotype of HBV. Of course, other methods such as serological methods may also be used.

In some embodiments, the presence or absence of the B or C genotype of HBV will be determined. In some embodiments, genotype B comprises 2733C, 1856C, 1009T and 2892T. Further, the subtype of genotype may also be determined. For example, in some embodiments, subtype C1 is characterized by 2733A, 1856C, 1099T and 2892T. In some embodiments, subtype C2 is identified by 2733C, 1856T, 1009T and 2892T. In some embodiments, subtype C3 is identified by 2733C, 1856C, 1009C and 2892T. The details are showed in the table below:

|  | 2733 | 1856 | 1009 | 2892 |
|---|---|---|---|---|
| B | C | C | T | T |
| C1 | A | C | T | T |
| C2 | C | T | T | T |
| C3 | C | C | C | T |
| Minor-cluster | C | C | C | C |

Detection of the nucleotides associated with a particular genotype may be detected by any method useful for detecting nucleotide sequences, including all of those described herein (e.g., amplification, nucleotide sequencing and/or probes, etc.).

IV. Comparing Nucleotides of HBV with Nucleotides Associated with HCC

Nucleotide sequence information regarding an isolate from an individual may be compared to nucleotides associated with HCC by any method.

Where a nucleotide sequence of the isolate is determined, the sequence may be aligned with SEQ ID NO:1 or another HBV genomic sequence to determine the position of the specific nucleotides of interest. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l Acad. Sci. USA* 85:2444 (1988), by computerized implementations of these algorithms (GAP, BEST-FIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

An example of algorithm that is suitable for aligning sequences and determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215: 403-410 (1990), respectively. BLAST and BLAST 2.0 may be used, with the parameters described herein, to determine an optimal alignment. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands and it is generally useful to turn off the complexity filter.

Positions of nucleotides of interest are provided throughout this application with reference to the first C of the first EcoR1 cleavage site (GAACTCC) that generally occur in the HBV genome. The first "C" is position 1 of SEQ ID NO:1. Thus, following alignment of a sequence of interest with SEQ ID NO:1, a particular nucleotide of the sequence of interest may be assigned a position relative to the corresponding position in the alignment with SEQ ID NO:1.

The presence of any of the following nucleotides is indicative of a pre-disposition for HCC: 31C, 53C, 312C, 799G, 961G, 1165T, 1499G, 1613A, 1762T, 1764A, 1899A, 2170C, 2170G, 2441C, 2525C, 2712C, 2712A, or 2712G. While those of skill in the art will recognize that any number of algorithms may be useful for predicting a predisposition for developing HCC, as described in the Example, particularly good sensitivity and specificity may be obtained using the following algorithm:

For genotype B HBV, the presence of:
1762T and 1764A and 2712A; or
1762T and 1764A and 2712C or;
1762T and 1764A and 2712G; or
1762T and 1764A and 2712T and 2525C; or
1762A and 1764G and 1165T, indicates a pre-disposition for HCC.

For genotype C1 HBV, the presence of:
31C; and/or
53C; and/or
1499G, indicates a pre-disposition for HCC.

For genotype C2 HBV, the presence of:
2170C; and/or
2170G; and/or
2441C; and/or
799G, indicates a pre-disposition for HCC.

For genotype C3 HBV, the presence of:
312C; and/or
961G; and/or
1613A; and/or
1899A, indicates a pre-disposition for HCC.

In some embodiments of the invention, it is useful to apply the above-listed algorithms in a computer readable form. The code for performing any of the functions described herein can be executed by the digital computers and may be stored on any suitable computer readable media. Examples of computer readable media include magnetic, electronic, or optical disks, tapes, sticks, chips, etc. The code for performing any of the functions described herein may also be written in any suitable computer programming language including, for example, Fortran, C, C++, etc. The graphical user interfaces and functions underlying the graphical user interfaces can be created using an object oriented programming language such as Java.

V. Benefits of Identifying Individuals Pre-Disposed for HCC

The conventional methods of surveillance for HCC are testing an infected person's serum alfa-fetoprotein levels (see, e.g., Liaw Y F et al., *Gastroenterology*, 30:263-267 (1986); Colombo M. et al, *N. Engl. J. Med.*, 325:675-680 (1991); Oka H. et al., *Hepatology* 12:680-687 (1990) or by subjecting the person to abdominal ultrasound scanning. Another method for diagnosis of HCC is detecting des-gamma-carboxy prothrombin (Chan C Y et al. *J Hepatol.* 13:21-24 (1991); Weitz I C et al., *Hepatology* 18:990-997 (1993)). Another marker for HCC is TGF-1β. See, e.g., US Patent Publication No. 2004/0121414.

However, without information regarding which patients may be pre-disposed for HCC, it is necessary to screen every person infected with HBV on a regular basis to catch HCC as early as possible. Unfortunately, given the large number of people infected with HBV, as well as the finite resources available to screen individuals, it is impossible to perform all of the necessary screens. The present invention addresses this problem, by indicating which individuals should have intense surveillance for the initial signs of HCC and which individuals do not require such intense surveillance. Thus, the present invention provides for detecting those individuals carrying HBV that is pre-disposed to cause HCC and then further testing those individuals on a regular basis for the presence of HCC and optionally, only rarely or never testing those individuals lacking HCC-associated HBV variants.

VI. Kits

Kits comprising the components needed in the methods (typically in an unmixed form) and kit components (packaging materials, instructions for using the components and/or the methods, one or more containers (reaction tubes, columns, etc.)) for holding the components are a feature of the present invention. Kits of the present invention may contain reagents for detecting any one or more of the following nucleotide variants in an HBV genome: 31C, 53C, 312C, 799G, 961G, 1165T, 1499G, 1613A, 1762T, 1764A, 1899A, 2170C, 2170G, 2441C, 2525C, 2712C, 2712A, and/or 2712G. For example, the kits of the invention may comprise combinations of primers and/or probes as described herein for the detection of nucleotide variants associated with HCC. Optionally, the kits may contain reagents for amplification, including but not limited to, thermostable polymerases such as Taq polymerase, nucleotides, buffers, etc.

EXAMPLE

Our goal was to discover genetic markers of HCC cases from HBV DNA sequences. In other words, we built up a classification model based on HBV DNA to predict cancer. Several classification models including Naive Bayes, Decision Tree, Neural Networks, and Rule Learning Using Evolutionary Algorithm, have been applied to classify the DNA datasets. The experimental results showed that the Rule Learning Using Evolutionary Algorithm has the best performance. In this section, we present the results of applying the Rule Learning Using Evolutionary Algorithm to classify the HBV DNA data in liver cancer (HCC) and normal cases.

Experimental Methodology

For each experiment, 90% of samples are selected randomly as the training set and the remains 10% samples form the testing set. For each dataset, the experiment is repeated for 10 times.

In medical diagnosis and disease predication problems, the algorithm or model performance is not only judged by accuracy, but also sensitivity and specificity. Sensitivity is generally more important than specificity and accuracy in medical diagnoses because doctors and patients prefer not to miss any patients with diseases. Extra diagnosis and tests can be performed to confirm their prediction and remove initial false positives.

We evaluated our model in all these three measurements.

$$Accuracy = \frac{True\ Positive + True\ Negative}{True\ Positive + True\ Negative}$$

$$Sensitivity = \frac{True\ Positive}{True\ Positive + False\ Negative}$$

$$Specificity = \frac{True\ Negative}{True\ Negative + False\ Positive}$$

The true positive is the number of all the patients with the disease and a positive test result, whereas the true negative is the number of all the patients without the disease and a negative test result. The false positive is the number of all the patients without the disease but a positive test result, whereas the false negative is the number of all the patients with the disease but a negative test result. In medical diagnosis, a false negative is the most undesirable case.

Results

Data Description

Genotype B and genotype C data were separated for analysis. The proportion of patients in each genotype or C subtypes is shown in Table 2. "CON" refers to "control," i.e., no HCC.

TABLE 2

| Datasets | CON | HCC | Total | % |
|---|---|---|---|---|
| B | 49 | 37 | 86 | 43.8776 |
| C1 | 10 | 16 | 26 | 13.2653 |
| C2 | 18 | 22 | 40 | 20.4082 |
| C3 | 19 | 25 | 44 | 22.4490 |
| Total | 96 | 100 | 196 | 100 |

Genotype B

Table 3 shows the details of the markers for HBV genotype B.

TABLE 3

| HBV markers for HCC of genotype B | | |
|---|---|---|
| Markers | Normal value | HCC-related value |
| 1762, 1764 | AG | TA |
| 1165 | C | T |
| 2712 | T | C (A, G) |
| 2525 | A, T | C |

The classification rules based on the applied data cleansing process for genotype B are as follows:

If 1762A and 1764G and 1165T are present in genotype B, then HCC is likely to occur.

If 1762T and 1764A and 2712A, 2712C or 2712G are present in genotype B, then HCC is likely to occur.

If 1762T and 1764A and 2712T and 2525C are present in genotype B, then HCC is likely to occur.

The experimental results for the genotype B dataset are shown in Table 4.

TABLE 4

Results of genotype B HBV dataset to predict HCC

| Results | Training set (STD) | Testing set (STD) |
|---|---|---|
| Sensitivity | 0.75029 (0.05361) | 0.75 (0.16667) |
| Specificity | 0.68 (0.06215) | 0.66 (0.13499) |
| Accuracy | 0.7093 (0.02615) | 0.70 (0.07499) |

C1 Subgroup

Table 5 shows the details of the markers for C1 subgroup.

TABLE 5

HCC related markers for C1 subgroup

| Markers | Normal value | HCC-related value |
|---|---|---|
| 31 | T | C |
| 53 | T | C |
| 1499 | A | G |

The classification rules based on the applied data cleansing process for C1 subgroup are as follows:

If 31C or 53C or 1499G are present in genotype C1, then HCC is likely to occur.

The Experimental results for the C1 subgroup are showed in Table 6.

TABLE 6

Results of genotype C1 HBV dataset to predict HCC

| Results | Training set (STD) | Testing set (STD) |
|---|---|---|
| Sensitivity | 0.80769 (0.04054) | 0.75 (0.26252) |
| Specificity | 0.7875 (0.06038) | 0.7 (0.48305) |
| Accuracy | 0.8 (0.03012) | 0.7333 (0.21082) |

C2 Subgroup

Table 7 shows the details of the markers for C2 subgroup.

TABLE 7

HCC related markers for C2 subgroup

| Markers | Normal value | HCC-related value |
|---|---|---|
| 2170 | T | C, G |
| 2441 | T | C |
| 799 | A | G |

The classification rules based on the applied data cleansing process for C2 subgroup are as follows:

If 2170C or 2170G or 2441C or 799G are present in genotype C2, then HCC is likely to occur.

The Experimental results on the C2 subgroup are showed in Table 8.

TABLE 8

Results of C2 genotype dataset to predict HCC

| Results | Training set (STD) | Testing set (STD) |
|---|---|---|
| Sensitivity | 0.84706 (0.06323) | 0.85 (0.24152) |
| Specificity | 0.97857 (0.0345) | 1 (0.00000) |
| Accuracy | 0.90645 (0.0355) | 0.925 (0.12076) |

The classification rules based on the applied data cleansing process for C3 subgroup are as follows:

If C312 or G961 or A1613 or A1899 are present in genotype C3, then HCC is likely to occur.

The Experimental results on the C3 subgroup are showed in Table 9.

TABLE 9

Results of C3 genotype dataset to predict HCC

| Results | Training set (STD) | Testing set (STD) |
|---|---|---|
| Sensitivity | 0.75 (0.0044) | 0.77 (0.22) |
| Specificity | 0.81 (0.0040) | 0.80 (0.26) |
| Accuracy | 0.77 (0.0024) | 0.78 (0.18) |

Patients and Methods

Patients

Residual serum samples of one hundred chronic hepatitis B patients suffering from hepatocellular carcinoma (HCC) and one hundred age-matched control patients who had chronic hepatitis B but without hepatocellular carcinoma were studied. Consecutive patients with confirmed diagnosis of HCC who had positive HBsAg attending the Joint Hepatoma Clinic, Prince of Wales Hospital from July 1999 to 2001 were included. Confirmed diagnosis of HCC is defined by either histology or radiological evidence of a hepatic mass with a serum alpha-fetoprotein (AFP) of 500 µg/l or more. Patients who had positive anti-HCV or history of alcoholism were excluded. Informed consent to provide serum sample for experimental study were routinely obtained from patients in Joint Hepatoma Clinic. Relevant clinical information of enrolled patients was collected retrospectively.

Age-matched control patients were identified from the cohort of chronic hepatitis B patients prospectively follow-up in the Hepatitis Clinic since December 1997. Patients who had other possible causes of hepatitis or liver cirrhosis including autoimmune liver disease, primary biliary cirrhosis, Wilson's disease and hemochromatosis were also excluded. At initial presentation, abdomen ultrasounds were performed to exclude any pre-existing HCC. Patients were prospectively followed up every 6 monthly, or more frequently if clinically indicated, with monitoring of liver biochemistry, HBeAg and anti-HBe status as well as alfa-fetoprotein levels. Abdomenal ultrasounds, computerized tomography, hepatic angiogram and/or liver biopsy were performed whenever alfa-fetoprotein level was higher than 50 µg/l or on a rising trend over 20 µg/l to confirm the diagnosis of HCC. For patients with normal alfa-fetoprotein levels, ultrasound abdomen was performed every 1-2 yearly.

Laboratory Method

Extraction of DNA

Serum viral DNA was extracted using QIAamp DNA Blood Mini Kit (Qiagen, CA, USA) according to the manufacturer's instructions.

Amplification of HBV DNA

To obtain the full-length HBV DNA sequence, a long distance semi-nested PCR was performed to amplify three overlapping fragments (A, B and C). Relative positions of these PCR fragments to the map of HBV genome are shown in FIG. 1 and the nucleotide sequences of the PCR primers can be found in Table 1.

TABLE 1

The sequences of primers used for amplifying and sequencing the HBV DNA

| Name | Nucleotide sequence (5'→3') | Nt positions | Direction |
|------|------------------------------|--------------|-----------|
| Primers used for PCR (SEQ ID NOS: 4-12) | | | |
| P1 | TTTTTCACCTCTGCCTAATCA | 1821-1841 | sense |
| P2 | CCCTAGAAAATTGAGAGAAGTC | 262-283 | antisense |
| P3[a] | CCACTGCATGGCCTGAGGATG | 3193-3213 | antisense |
| P4 | GCCTCATTTTGTGGGTCACCATA | 2801-2824 | sense |
| P5 | TTCTTTGACATACTTTCCA | 979-997 | antisense |
| P6[a] | TTGGGGTGGAGCCCTCAGGCT | 3070-3090 | sense |
| P7[a] | TTGGCCAAAATTCGCAGTC | 300-318 | sense |
| P8[a] | CCCCACTGTTTGGCTTTCAG | 714-734 | sense |
| P9[a] | GTTGATAAGATAGGGGCATTTGGTGG | 2299-2325 | antisense |
| Primers used for sequencing (SEQ ID NOS: 13-21) | | | |
| S1 | CTCCGGAACATTGTTCACCT | 2031-2050 | sense |
| S2 | AAGGTGGGAAACTTTACTGGGC | 2469-2490 | sense |
| S3 | GCTGACGCAACCCCCACTGG | 1186-1205 | sense |
| S4 | TCGCATGGAGACCACCGTGA | 1604-1623 | sense |
| S5 | GGCAAAAACGAGAGTAACTC | 1940-1959 | antisense |
| S6 | GGGTCGTCCGCGGGATTCAG | 1441-1460 | antisense |
| S7 | GACATACTTTCCAATCAATAGG | 970-991 | antisense |
| S8 | GAAGATGAGGCATAGCAGCAGG | 411-433 | antisense |
| S9 | CATGCTGTAGCTCTTGTTCC | 2831-2850 | antisense |

[a]These primers were also used for sequencing.

Fragment A

When amplifying fragment A, 5 µl of the extracted DNA was subjected to PCR in the presence of 50 mM KCl, 1.5 mM MgCl$_2$, 10 mM Tris-HCl, 200 µM of each dNTP, 1.25 units Taq DNA polymerase (Amersham Biosciences), 1.5 units pfu DNA polymerase (Promega), and 10 pmol of each P1 primer and P2 primer in a final volume of 50 µl. PCR was carried out under a 5-min initial denaturation at 95° C., followed by 10 cycles of amplification (94° C., 36 sec; 60° C., 36 sec; 72° C., 2.5 min) and then 30 cycles of amplification (94° C., 36 sec; 50° C., 36 sec; 72° C., 2.5 min) and 7-min final extension at 72° C.

The PCR product was further amplified in a semi-nested PCR. One microliter of the product was subjected to PCR in the presence of 50 mM KCl, 1.5 mM MgCl$_2$, 10 mM Tris-HCl, 200 µM of each dNTP, 2.5 units Taq DNA polymerase (Amersham Biosciences) and 10 pmol of each P1 primer and P3 primer in a final volume of 50 µl. PCR was carried out under a 5-min initial denaturation at 95° C., followed by 10 cycles of amplification (94° C., 36 sec; 60° C., 36 sec; 72° C., 2 min) and then 30 cycles of amplification (94° C., 36 sec; 52° C., 36 sec; 72° C., 2 min) and a 7-min final extension at 72° C. Finally, quality and quantity of the PCR product was examined on a 1.0% agarose/EtBr gel run in 1×TBE buffer.

Fragment B

When amplifying fragment B, 5 µl of the extracted DNA was subjected to PCR in the presence of 50 mM KCl, 1.5 mM MgCl$_2$, 10 mM Tris-HCl, 200 µM of each dNTP, 1.25 units Taq DNA polymerase (Amersham Biosciences), 1.5 units pfu DNA polymerase (Promega), and 10 pmol of each P4 primer and P5 primer in a final volume of 50 µl. PCR was carried out under a 5-min initial denaturation at 95° C., followed by 10 cycles of amplification (94° C., 36 sec; 60° C., 36 sec; 72° C., 90 sec) and then 30 cycles of amplification (94° C., 36 sec; 50° C., 36 sec; 72° C., 90 sec) and a 7-min final extension at 72° C.

The PCR product was further amplified in a semi-nested PCR. One microliter of the product was subjected to PCR in the presence of 50 mM KCl, 1.5 mM MgCl$_2$, 10 mM Tris-HCl, 200 µM of each dNTP, 2.5 units Taq DNA polymerase (Amersham Biosciences) and 10 pmol of each P5 primer and P6 primer in a final volume of 50 µl. PCR was carried out under a 5-min initial denaturation at 95° C., followed by 10 cycles of amplification (94° C., 36 sec; 60° C., 36 sec; 72° C., 90 sec) and then 30 cycles of amplification (94° C., 36 sec; 52° C., 36 sec; 72° C., 90 sec) and a 7-min final extension at 72° C. Finally, quality and quantity of the PCR product was examined on a 1.0% agarose/EtBr gel run in 1×TBE buffer.

Fragment C

When amplifying fragment C, 5 µl of the extracted DNA was subjected to PCR in the presence of 50 mM KCl, 1.5 mM MgCl$_2$, 10 mM Tris-HCl, 200 µM of each dNTP, 1.25 units Taq DNA polymerase (Amersham Biosciences), 1.5 units pfu DNA polymerase (Promega), and 10 pmol of each P7 primer and P9 primer in a final volume of 50 µl. PCR was carried out under a 5-min initial denaturation at 95° C., followed by 10 cycles of amplification (94° C., 36 sec; 60° C., 36 sec; 72° C., 2 min and 15 sec) and then 30 cycles of amplification (94° C., 36 sec; 50° C., 36 sec; 72° C., 2 min and 15 sec) and a 7-min final extension at 72° C.

The PCR product was further amplified in a semi-nested PCR. One microliter of the product was subjected to PCR in the presence of 50 mM KCl, 1.5 mM MgCl$_2$, 10 mM Tris-HCl, 200 µM of each dNTP, 2.5 units Taq DNA polymerase (Amersham Biosciences) and 10 pmol of each P8 primer and P9 primer in a final volume of 50 µl. PCR was carried out under a 5-min initial denaturation at 95° C., followed by 10 cycles of amplification (94° C., 36 sec; 60° C., 36 sec; 72° C., 1 min and 50 sec) and then 30 cycles of amplification (94° C., 36 sec; 52° C., 36 sec; 72° C., 1 min and 50 sec) and a 7-min final extension at 72° C. Finally, quality and quantity of the PCR product was examined on a 1.0% agarose/EtBr gel run in 1×TBE buffer.

DNA Sequencing

All semi-nested PCR products (plus and minus strands) were directly sequenced with the Cycling Sequencing Kit DYEnamic ET Dye terminator for MegaBACE (Amersham Biosciences).

Primers for the sequencing of three HBV DNA fragments (primers sequences are listed in Table 1):
Fragment A: S1, S2, P3, S9
Fragment B: P6, P7, S7, S8
Fragment C: P8, S3, S4, P9, S5, S6

One microliter of unpurified PCR product was used as the DNA template for cycle sequencing. It was subjected to sequencing reaction in the presence of 8 µl of DYEnamic ET reagent premix and 10 pmol primer in a final volume of 20 µl. Sequencing reaction mix was subjected to a 2 min initial denaturation at 95° C., followed by 30 cycles at 95° C., 25 sec; 52° C., 30 sec; 60° C.; 60 sec.

The sequencing products were purified by post reaction clean up using ethanol precipitation. In each reaction tube, 2 µl of 7.5M ammonium acetate and 2.5 volumes (55 µl) of 100% ethanol were added so that the final concentration of ethanol was 70%. Then it was subjected to centrifugation at 4,000 rpm for 30 min at 14° C. Afterwards, the supernatant was drawn off by performing a brief inverted spin (1 min at 500 rpm). The DNA pellet was washed by 100 µl of 70% ethanol. Then, it was subjected to centrifugation at 4,000 rpm for 15 min at 14° C. and the supernatant was drawn off by performing a brief inverted spin (1 min at 500 rpm). Then the DNA pellet was allowed to air dry and was resuspended in 10 µl of loading buffer (70% formamide and 1 mM EDTA). The samples were stored at 4° C. before gel electrophoresis analysis using the MegaBACE 1000 DNA sequencer.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of determining a pre-disposition of an individual infected with hepatitis B virus (HBV) to develop hepatocellular carcinoma (HCC), the method comprising:
   a) determining a nucleotide in the genome of HBV isolated from the individual at at least the position corresponding to nucleotide 31 of SEQ ID NO:1; and
   b) determining the presence or absence of 31C in the HBV genome, wherein if the HBV genome has 31C, the individual has a predisposition to develop HCC.

2. The method of claim 1, wherein the determining step b) comprises aligning a nucleotide sequence from the HBV isolated from the individual to SEQ ID NO:1 to determine the position of the nucleotide in the nucleotide sequence corresponding to position 31 with 31C.

3. The method of claim 2, wherein the aligning step is performed on a computer.

4. The method of claim 1, further comprising c) providing a prognosis of HCC predisposition based on the results of step b).

5. The method of claim 4, wherein the HBV genome has 31C.

6. The method of claim 5, further comprising testing the individual for the presence of HCC.

7. The method of claim 1, further comprising determining the genotype of the HBV from the individual.

8. The method of claim 1, the method further comprising determining nucleotides in the genome of a genotype C HBV isolated from the individual at positions corresponding to nucleotides 53, 312, 799, 961, 1499, 1613, 1899, 2170, or 2441; and comparing the determined nucleotides to nucleotides associated with a pre-disposition to cause HCC, wherein the nucleotides associated with a pre-disposition to cause HCC comprise: 53C, 312C, 799G, 961G, 1499G, 1613A, 1899A, 2170C, 2170G, or 2441C.

9. The method of claim 8, the method comprising
a) determining the subtype of a genotype C HBV from the individual, wherein:
subtype C1 comprises nucleotides 2733A, 1856C, 1009T and 2892T;
b) if the HBV is genotype C1, further determining the nucleotides at positions corresponding to nucleotides 53 or 1499 of SEQ ID NO:1; and
c) comparing the determined nucleotides to nucleotides at the positions associated with a pre-disposition to cause HCC, wherein the nucleotides associated with a pre-disposition to cause HCC in subtype C1 comprise:
53C; or
1499G.

10. The method of claim 9, wherein the determining step comprises nucleotide sequencing the HBV genome flanking the nucleotides at positions corresponding to nucleotides 31, 53, and 1499 of SEQ ID NO:1.

11. The method of claim 9, wherein the determining step comprises amplifying at least a portion of the HBV genome to produce one or more amplification products comprising the nucleotides at the positions corresponding to nucleotides 31, 53, and 1499 of SEQ ID NO:1.

12. The method of claim 11, comprising contacting the one or more amplification products with one or more probes that hybridize to nucleotides:
31C, 53C, or 1499G;
under conditions to allow for hybridization of a probe to an amplification product only if the amplification product comprises a complementary nucleotide at the position of 31C 53C, or 1499G.

13. The method of claim 12, wherein the hybridization is performed as a line probe assay.

14. The method of claim 9, further comprising determining the genotype of the HBV from the individual.

* * * * *